(12) United States Patent
Fercher et al.

(10) Patent No.: US 8,437,008 B2
(45) Date of Patent: May 7, 2013

(54) INTERFEROMETRIC SAMPLE MEASUREMENT

(75) Inventors: Adolf Friedrich Fercher, Vienna (AT); Rainer Leitgeb, Vienna (AT)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 13/184,947

(22) Filed: Jul. 18, 2011

(65) Prior Publication Data

US 2011/0292395 A1 Dec. 1, 2011

Related U.S. Application Data

(62) Division of application No. 12/096,348, filed as application No. PCT/EP2006/011738 on Dec. 6, 2006, now Pat. No. 7,982,881.

(30) Foreign Application Priority Data

Dec. 6, 2005 (DE) .................. 10 2005 058 220
Aug. 16, 2006 (AT) .................. A 1374/2006

(51) Int. Cl.
*G01B 11/02* (2006.01)
*A61B 3/10* (2006.01)

(52) U.S. Cl.
USPC ............................. 356/497; 351/221

(58) Field of Classification Search .......... 356/477, 356/479, 497; 250/227.19, 227.27; 351/210, 351/221
See application file for complete search history.

(56) References Cited

U.S. PATENT DOCUMENTS 5,064,289 A 11/1991 Bockman
6,198,540 B1 3/2001 Ueda et al.
6,256,102 B1 7/2001 Dogariu
6,377,349 B1 4/2002 Fercher
6,755,819 B1 6/2004 Waelti
6,806,963 B1 10/2004 Wälti et al.
7,126,693 B2 10/2006 Everett et al.
7,400,410 B2 7/2008 Baker et al.
7,480,058 B2 * 1/2009 Zhao et al. .................. 356/497

(Continued)

FOREIGN PATENT DOCUMENTS

AT 500 501 A1 1/2006
DE 198 14 057 A1 10/1999

(Continued)

OTHER PUBLICATIONS

Fercher, Adolf F., "Optical Coherence Tomography," *J. Biomedical Optics*, Vo. 1, No. 2, pp. 157-173 (Apr. 1996).

(Continued)

*Primary Examiner* — Michael A Lyons
(74) *Attorney, Agent, or Firm* — Patterson Thuente Pedersen, P.A.

(57) ABSTRACT

A device for the interferometric measurement of a sample, in particular the eye, including an interferometer arrangement with a first measurement beam path, through which a measurement beam falls onto the sample, and a first reference beam path, through which a reference beam runs, which is applied to the measuring beam for interference. The interferometer arrangement includes a second measuring beam path and/or second reference beam path. The optical path lengths of the second measuring beam path and/or second reference beam path are different from one of the first beam paths. The wave length difference is selected according to a distance of two measuring areas which are arranged at a distance in the depth direction of the sample.

2 Claims, 18 Drawing Sheets

U.S. PATENT DOCUMENTS

| | | | |
|---|---|---|---|
| 7,710,577 | B2 | 5/2010 | Yatagai et al. |
| 2005/0056787 | A1* | 3/2005 | Cong et al. .................... 250/343 |
| 2005/0140981 | A1 | 6/2005 | Waelti |
| 2005/0219544 | A1 | 10/2005 | Chan et al. |
| 2007/0013918 | A1 | 1/2007 | Hauger et al. |
| 2007/0165234 | A1 | 7/2007 | Podoleanu |

FOREIGN PATENT DOCUMENTS

| | | |
|---|---|---|
| EP | 1 582 143 A1 | 10/2005 |
| EP | 1 602 320 A1 | 12/2005 |
| WO | WO 01/19303 A1 | 3/2001 |
| WO | WO 01/38820 A1 | 5/2001 |
| WO | WO 03/062802 A2 | 7/2003 |
| WO | WO 03/086180 A2 | 10/2003 |
| WO | WO 2004/043245 A1 | 5/2004 |
| WO | WO 2005/040718 A1 | 5/2005 |
| WO | WO 2006/015717 A1 | 2/2006 |

OTHER PUBLICATIONS

Podoleanu, Adrian Gh., et al., "Fiberised Set-Up for Eye Length Measurement," *Optics Communications*, vol. 137, pp. 397-405 (May 1997).

Wojtkowski, Maciej, et al., "In Vivo Human Retinal Imaging by Fourier Domain Optical Coherence Tomography," *J. Biomedical Optics*, vol. 7, No. 3, pp. 457-463 (Jul. 2002).

Fercher, A.F., et al., "Optical Coherence Tomography—Principles and Applications," *Reports on Progress in Physics, Institute of Physics Publishing*, vol. 66, pp. 239-303 (2003).

*Intralase Product Leaflet*, Essential Technology for Biomechanical Stability, Intralase Corp., 6 pgs. (2006).

Application and File History of U.S. Appl. No. 12/096,348, Inventors Adolf Friedrich and Rainer Leitgeb, filed Jun. 5, 2008, now U.S. Patent No. 7,982,881, issued Jul. 19, 2011.

\* cited by examiner

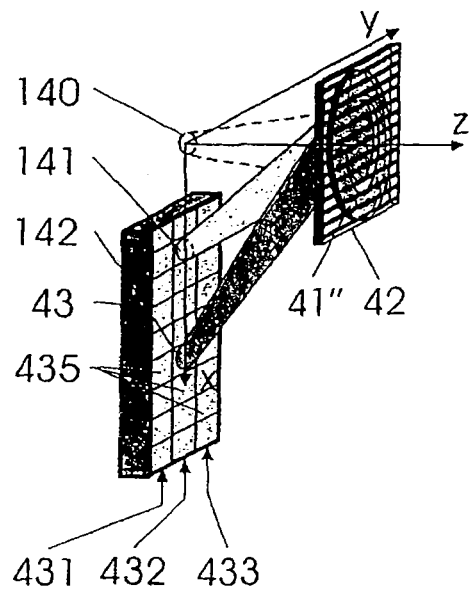
Figure 4
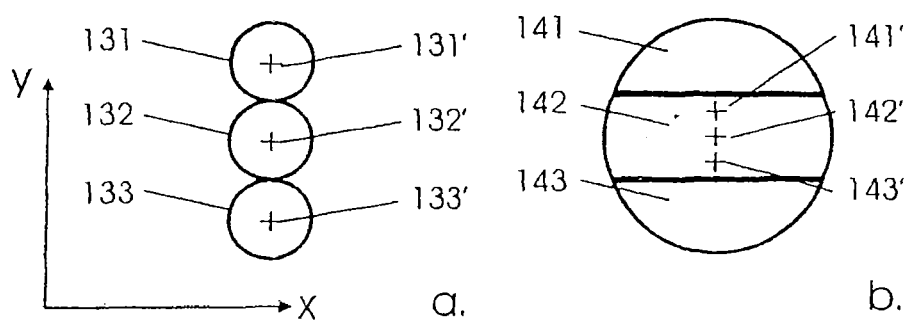
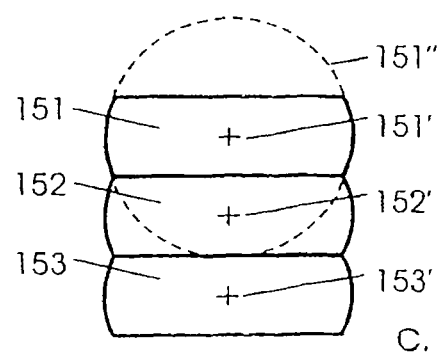
Figure 5

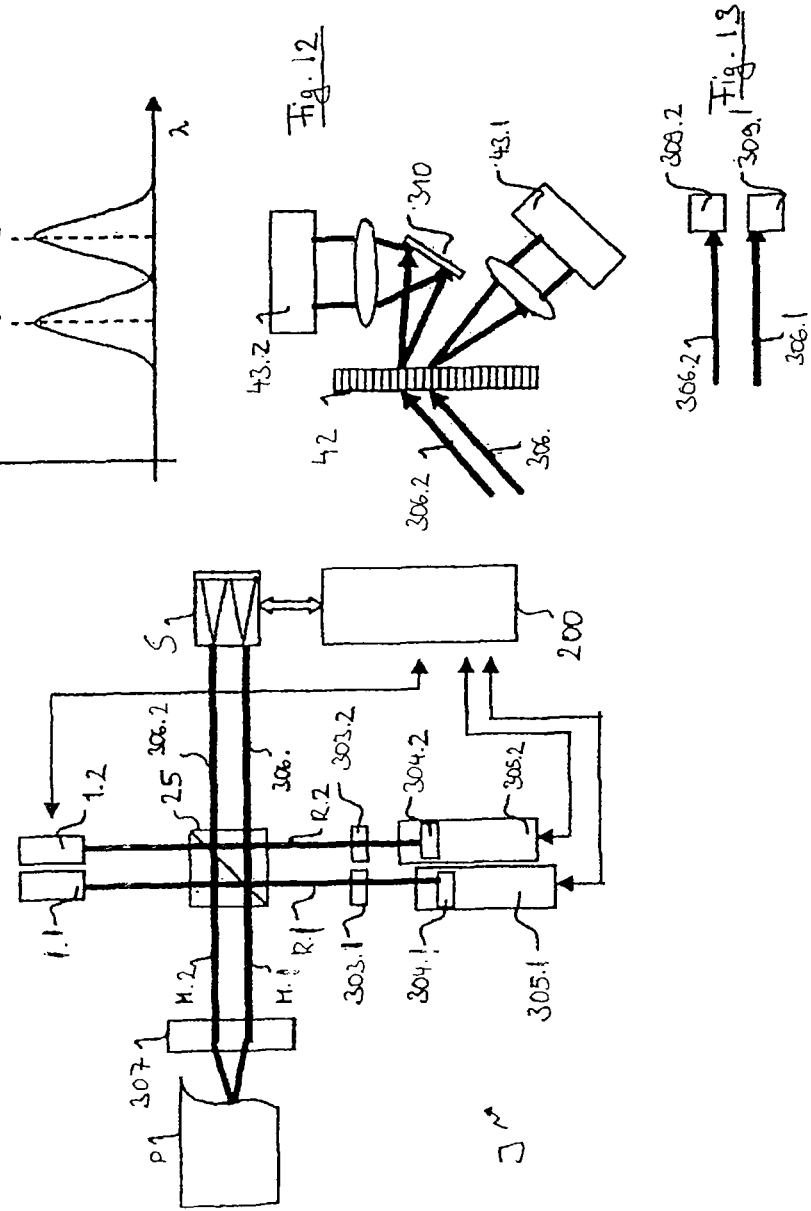

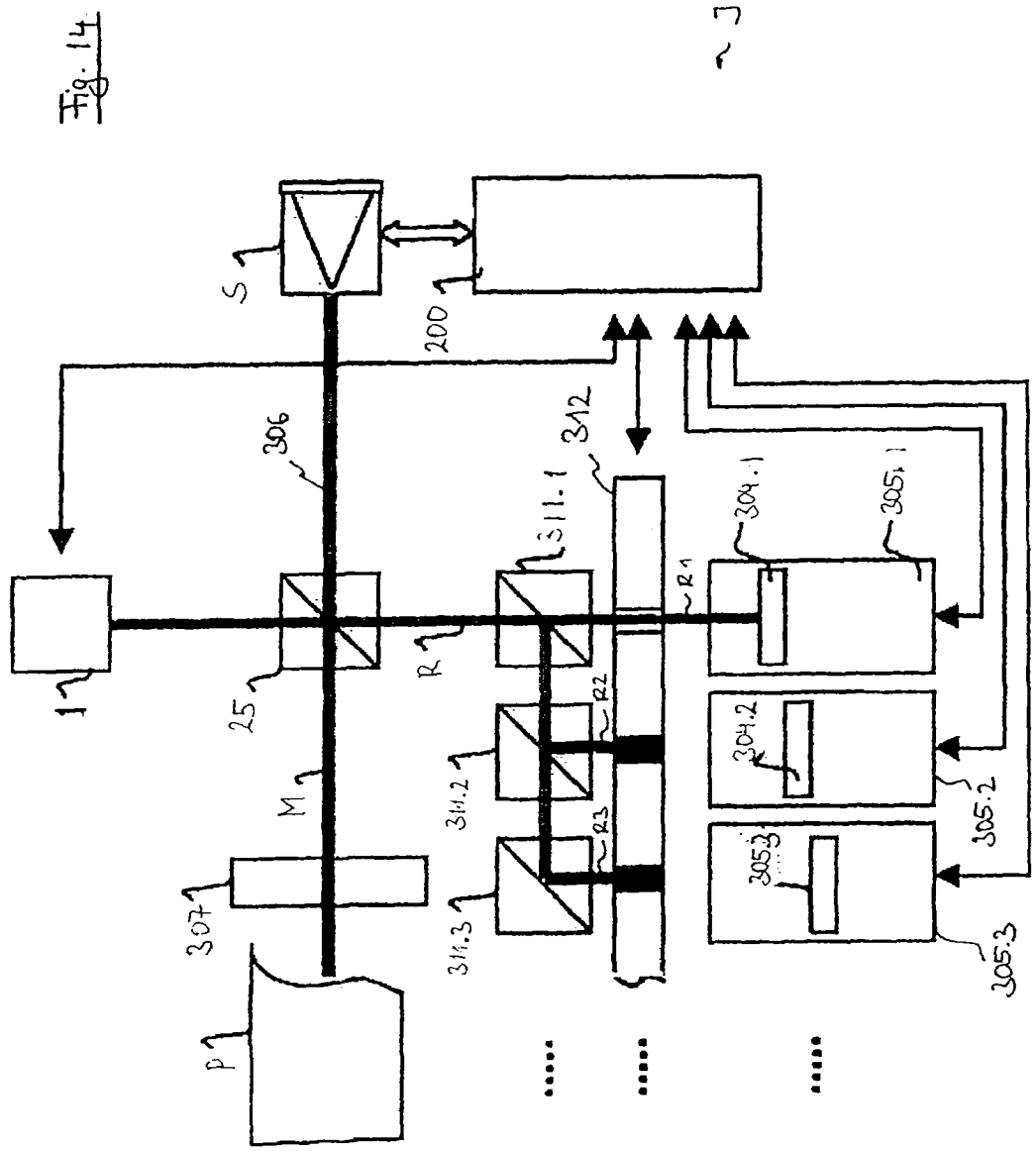

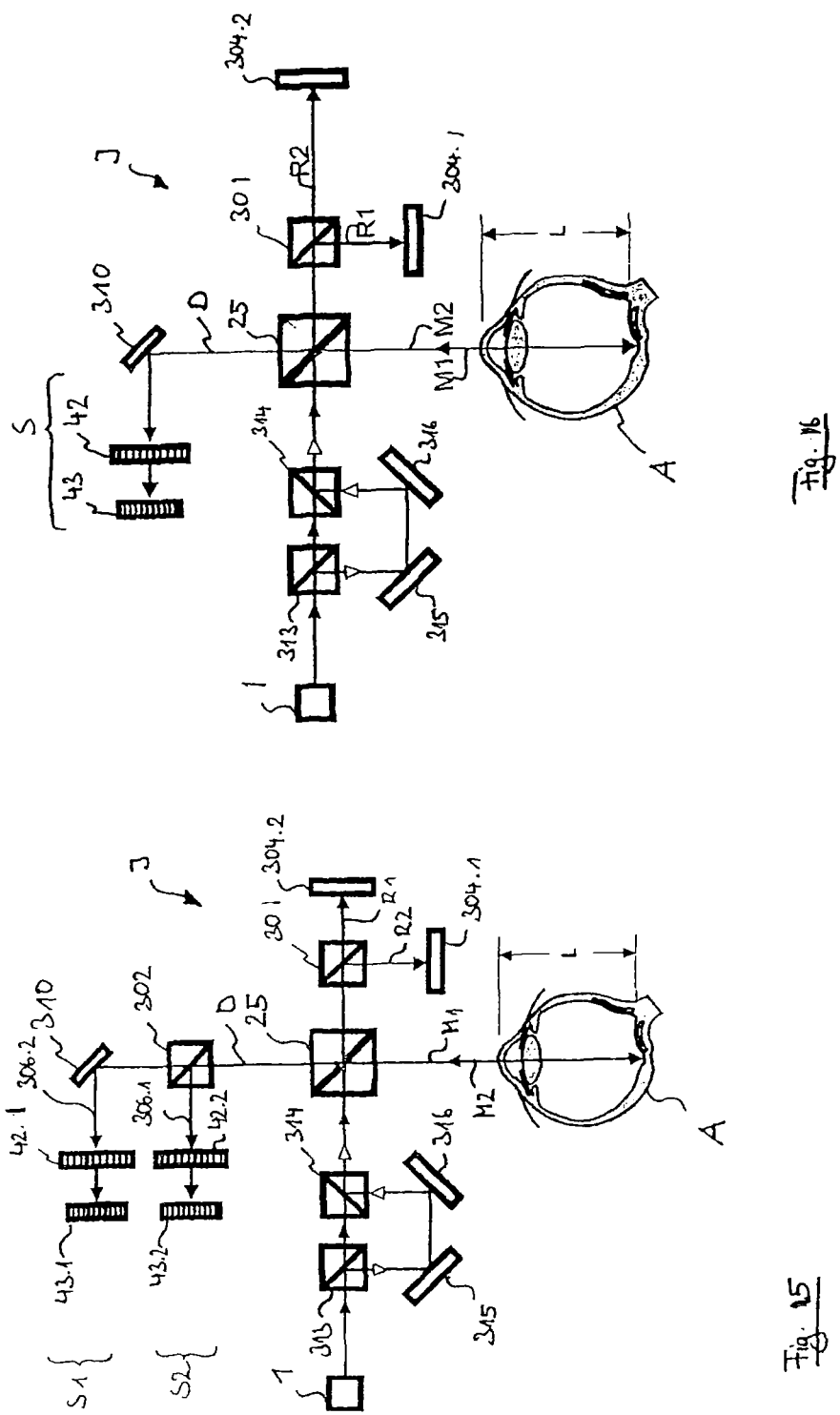

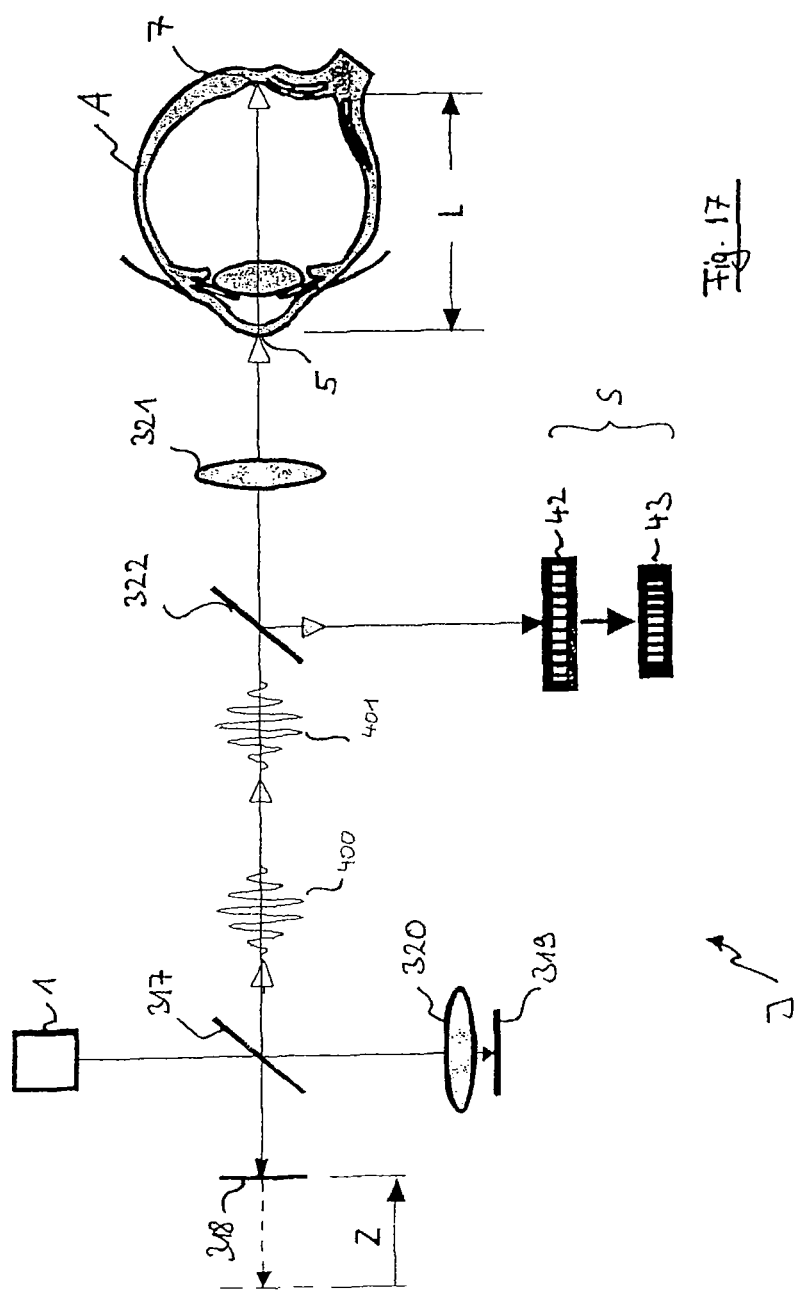

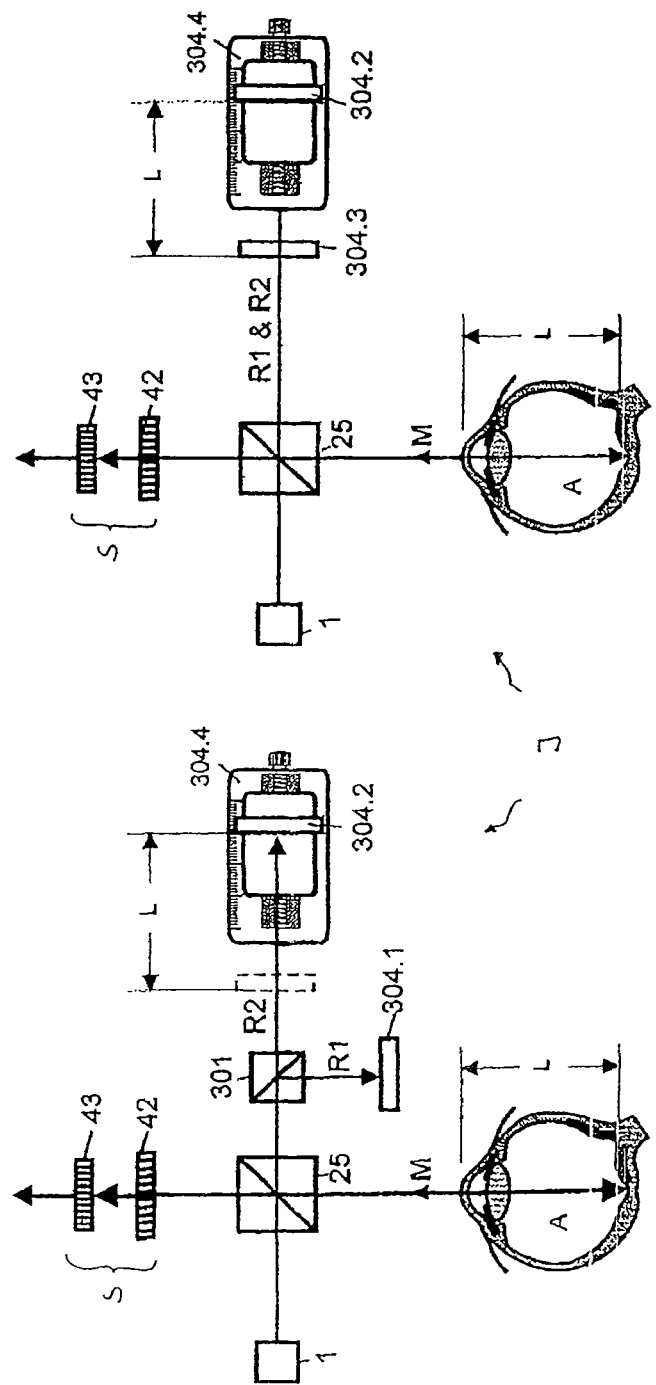

INTERFEROMETRIC SAMPLE MEASUREMENT

This application is a divisional application of application Ser. No. 12/096,348, filed Jun. 5, 2008 (U.S. Pat. No. 7,982,881 issuing Jul. 19, 2011), which application is a 371 of PCT/EP2006/011738, filed Dec. 6, 2006, which claims the benefit of AT application number A1374/2006, filed Aug. 16, 2006 and claims the benefit of DE application number 102005058220.6, filed Dec. 6, 2005. Said applications are herein incorporated by reference herein in their entirety.

The invention relates to an apparatus for interferometric measurement of a sample, in particular of the eye, said apparatus comprising a short-coherence interferometer arrangement, which comprises a measurement beam path through which a measurement beam is incident on the sample, and a reference beam path, through which a reference beam passes that is superimposed upon and made to interfere with the measurement beam. The invention further relates to a method for short-coherence interferometric measurement of a sample, in particular of the eye, wherein a measurement beam is directed onto the sample through a first measurement beam path and is superimposed upon a reference beam, which passes through a reference beam path, and made to interfere with said reference beam.

For interferometric measurement or surveillance of samples, optical short-coherence tomography (also called OCT) is known. This principle allows to optically measure cuts in the material in a highly sensitive manner, achieving axial resolutions, i.e. resolutions along the optical axis of incidence of the radiation, of few micrometers. The principle is based on optical interferometry and uses a partially coherent light source for resolution in depth direction, i.e. along the optical axes.

A known application for optical coherence tomography is that of measuring the eye, in particular the human eye. Carl Zeiss Meditec AG distributes a device for this purpose, which is called IOL Master and determines, inter alia, the eye length, i.e. the distance between the corneal vertex and the fundus. In doing so, the path length of the reference beam is modified during measurement. The device is applied, in particular, in connection with cataract surgery. In cataract surgery and refractive ophthalmic surgery, the refractive power of an intraocular lens to be implanted is determined on the basis of the pre-operative refractive condition of the eye, of the acoustically or optically determined length of the eye and of an estimation of the post-operative anterior chamber depth. Thus, precise knowledge of these parameters is required prior to the operation. The scanning process of the IOL Master provides a signal at the interferometer output, and the lengths to be measured are determined from the time course of the signal. This scanning process takes time; movements of the subject during measurement lead to errors or inaccurate results.

Further, a Fourier analysis interference method is known. For spatial resolution in depth direction, a spectrum of the interference pattern between the reference beam and the measurement beam scattered back from the sample is recorded. Recording can be effected simultaneously, using a spectrometer (for a suitable broadband light source), or sequentially (for spectrally sweepable sources). The inverted Fourier transform of the spectrum enables reconstruction of the structure along the depth direction.

Therefore, it is an object of the invention to improve an apparatus of the above-mentioned type such that larger partial lengths of the eye can be rapidly measured.

The invention achieves said object in that the interferometer arrangement is pre-tuned to different, axially spaced sample regions with respect to the lengths of the reference beam paths. Reference beam paths are spatially separated and have different lengths, with the path length difference defining a distance of the measurement regions in the sample. The OCT measurement then measures only the deviation from the pre-set distance. The radiation from the respective reference beam path is automatically superimposed upon the measurement beam and detected.

Thus, the invention utilizes, for example, Fourier domain short-coherence interferometry (FD OCT), which exploits the wave number spectrum of the signal at the interferometer output. This spectrum is recorded, for example, using a spectrometer which usually contains a dispersing element, for example a diffraction grating, and focusing optics as well as a detector array, e.g. photodiode arrays or array cameras. The wavelength spectrum $I(\lambda)$ registered by the detector array is converted into the required signal spectrum or K spectrum $I(K)$, for example, using the grating equation. The scan carried out electronically by typical photodiode arrays or array cameras is very quick and only takes few milliseconds or fragments of a millisecond. The same applies to the wavelength sweeping of radiation sources, when working with spectrally non-selective detectors. Thus, a "one-shot" quality is achieved by which the relevant measurement data are obtained from one single or very short illumination of the eye and which is advantageous for measurements on patients.

Fourier transformation of the K spectrum provides a depth-dependent signal with signal peaks whose z positions indicate the path difference between reference beam and measurement beam.

The resolution $\Delta z$ of short-coherence interferometry is related to the half width $\Delta\lambda$ of the wavelength spectrum and to its average wavelength $\bar{\lambda}$. For a Gaussian spectrum, one obtains:

$$\Delta z = \frac{2\ln}{\pi} \cdot \frac{\bar{\lambda}^2}{\Delta \lambda}$$

The measurement field depth Z is limited by the pixel number or the number N of array photodiodes in the dispersion direction of the spectrometer or by the number of recordings made during tuning. In this case, $$N = \Delta K \cdot \frac{Z}{\pi}$$

holds true, when $\Delta K$ is the bandwidth of the optical radiation of use in the K space. Thus, the measurement field depth is $$Z = \frac{N\bar{\lambda}^2}{4\Delta\lambda}.$$

The measurement field depth depends linearly on the pixel number N of the spectrometer or on the number of recordings. Usual array pixel numbers of N≈1,000 provide a measurement field depth Z of around 5.3 mm. The origin of the measurement field is the "zero path difference position", i.e. that position in the measurement beam at which the optical length of the measurement beam equals that of the reference beam.

The invention can be realized by an apparatus for interferometric measurement of a sample, in particular the eye, said apparatus comprising a short-coherence interferometer arrangement, which includes a measurement beam path through which a measurement beam is incident on the sample and a first reference beam path through which a reference beam passes, said reference beam being superimposed upon and made to interfere with the measurement beam, said interferometer arrangement comprising at least one second reference beam path, which is spatially separated, at least partially, from the first reference beam path and whose optical path length differs from that of the first reference beam path, with the path length difference being selected according to a distance of two sample regions which are spaced apart in depth direction of the sample, and with a control device determining from the detected, superimposed beams the distance between the sample regions by a Fourier spectral analysis in consideration of the path length difference of the reference beam paths. The invention can be analogously realized by a method for short-coherence interferometric measurement of a sample, in particular of the eye, wherein a measurement beam is directed onto the sample through a measurement beam path and is superimposed and made to interfere with a reference beam that passes through a first reference beam path, wherein at least one second reference beam path is provided, which is at least partially separated from the first reference beam path and whose optical path length differs from that of the first reference beam path, the path length difference being selected according to a distance between two sample areas which are spaced apart in depth direction of the sample, and the superimposed radiation being detected and used to determine the distance between the sample areas by a Fourier spectral analysis in consideration of the path length difference of the reference beam paths.

It is advantageous for the signal quality to separately effect superposition and detection of the measurement radiation reflected back by the sample upon the radiations from both reference beam paths in the interferometer arrangement. Therefore, a further embodiment provides for the interferometer arrangement to comprise a superimposing device, which separately superimposes the measurement beam from the measurement beam path upon the reference beams from the two reference beam paths and transmits each beam thus superimposed to a detector device for detection, said detector device generating measurement signals which are assigned to the spaced-apart measurement regions. Analogously, the method provides for the beams from the two reference beam paths to separately have the measurement beam from the measurement beam path superimposed upon them, to separately detect each superimposed beam, and to generate measurement signals assigned to the spaced-apart measurement regions.

Separation in the case of superposition and detection can be effected in different manners. On the one hand, a separation in time is possible. Thus, the measurement beam has the reference beams from the reference beam path sequentially superimposed upon it and is also detected in sequence. This has the advantage that only one detector unit is necessary, at the cost of a somewhat longer measurement time. Since only one spectral analysis apparatus is necessary on the detection side, complexity and, thus, costs can be considerably reduced. Therefore, one variant of the invention provides for the superimposing device to comprise a switching mechanism for switching between the two reference beam paths such that superposition is effected sequentially for the two reference beam paths. Analogously, the method provides for sequential switching between the two reference beams such that the measurement beam sequentially has radiation from the first and second reference beam paths superimposed upon it and the superimposed beams are sequentially detected.

On the other hand, a higher measurement speed is achieved, if said superposition is such that the separately superimposed beams, i.e. the interference patterns generated for the different measurement regions, are detected in parallel. A first approach uses polarization separation. Thus, for example, two reference beam paths are provided, guiding mutually orthogonally polarized radiations. On the detection side, there are also provided two detector units, which also evaluate mutually orthogonal radiation components of the superimposed radiation. Therefore, it is convenient for this first variant that the superimposing device uses polarization separation to separate superposition such that superposition and transmission to the detector device are effected simultaneously for the two reference beam paths, separated according to their polarizations. Further, it is convenient for the method to use polarization separation to separate superposition such that separate superposition and detection are effected simultaneously for the two reference beam paths, separated according to their polarizations.

A second variant yields a further separation possibility by the use of different wavelength regions. The reference beam paths can then be coupled with each other by dichroic splitting of the incident reference radiation, and a corresponding number of detector devices follows a corresponding dichroic separation. Therefore, it is convenient for this second variant that the superimposing device uses dichroic separation to separate superposition such that superposition and transmission to the detector device are effected in a spectrally separated and simultaneous manner for the two reference beam paths. Analogously, this method provides for the use of a dichroic separation to separate superposition such that separate superposition and detection are effected in a spectrally separate and simultaneous manner for the two reference beam paths.

A further separation enabling simultaneous measurement consists in a spatial separation of the superimposed radiation. In this third variant, the measurement radiation spatially diverges and is superimposed upon corresponding spatially separated reference beams from the reference beam paths. The spatial separation may be realized, in particular, by pupil partition. Therefore, a further embodiment provides that the superimposing device for separate superposition use pupil partition such that superposition and transmission to the detector device for the two reference beam paths is effected in a parted pupil of the beam path.

As already mentioned, the concept according to the invention uses short-coherence FD OCT. In doing so, the required K spectrum can be generated using both spectrally sensitive detection and broadband sources as well as spectrally non-resolving detection and wavelength sweeping of a narrow-band source. Of course, the detector's complexity is reduced if a radiation source, which feeds the interferometer arrangement and is spectrally sweepable, and a spectrally non-resolving detector device are provided for measurement. The K spectrum is composed here using the tuning data and is then analyzed.

In FD OCT there used to be the problem that, using the available detectors with a predetermined maximum number of pixels or recordings per time unit, either the spectral resolution and, thus, the spatial resolution, or the spectral range covered, i.e. the measurement range, could be maximized. Now, the concept according to the invention overcomes this negative interlinking by using several reference beam paths of different lengths.

The measured distances usually refer to the distance from the interferometer or from the zero path difference position already mentioned above. In a further embodiment, it is possible to refer these measurement signals to each other. This is effected in that the reference beam path no longer effects reflection at a static reflector built into the interferometer, but uses as the reference beam a beam incident on the sample and reflected or scattered back there. Therefore, in connection with the above mentioned interferometer arrangement, the invention also provides for the reference beam path to comprise the sample, with the reference beam and the measurement beam being offset by a specific path length difference relative to each other in the beam direction, the reference beam being reflected and/or scattered back at a first sample region and the measurement beam being reflected and/or scattered back at a second sample region of the sample, and the interference between the measurement beam and the reference beam depending on the distance between the two sample regions, with a control device determining the distance of the sample regions on the basis of the detected, superimposed beams by means of Fourier spectral analysis in consideration of the path length difference of the reference beam paths. Analogously, the method provides for the reference beam path to comprise the reference beam and the measurement beam, mutually offset in the beam direction by a specific path length difference, and the reference beam being reflected and/or scattered back at a first sample region and the measurement beam being reflected and/or scattered back at a second sample region, and the distance between the two sample regions being determined from the interference between the measurement and reference beams, for which purpose the superimposed radiation is detected and used to determine the distance of the sample regions by means of Fourier spectral analysis in consideration of the path length difference between the reference beam paths.

When measuring the eye, it is convenient, of course, to evaluate the back reflection of the anterior corneal surface, because the eye length can thus be measured in a particularly simple manner. The autocorrelation function of the reference beam provides a first reference point for evaluation, and the superposition of the measurement beam on the reference beam provides a second measurement point referred to this reference point, said second measurement point being, for example, the signal for the fundus of the eye.

When measuring the eye, it is convenient to provide a focusing element in one of the beam paths in order to ensure focusing of both beams on the cornea and on the fundus of the eye. Thus, the focusing element takes the focusing effect of the eye into consideration so that the measurement beam focused on the fundus is incident on the eye as a parallel ray bundle, whereas the other reference beam is already focused on the anterior surface of the eye. Of course, the focusing element can be provided in the measurement beam path (for expansion) or in the reference beam path (for collimation). This approach considerably raises the signal level. Therefore, it is convenient for the reference or measurement beam paths to comprise a preferably adjustable focusing element in order to focus the measurement beam on the retina for eye measurements. It is likewise advantageous for the analogous method to focus the reference beam onto the cornea by means of a preferably adjustable focusing element for eye measurements.

During passage through the eye, a dispersing influence may appear, which may have an interfering effect. Therefore, it is convenient to provide for a corresponding dispersion compensation. Thus, it is conveniently ensured in the apparatus that the measurement path or the reference beam path comprises a dispersion-compensating element so that, for eye measurements, the eye's dispersing influences on the measurement beam are compensated for. It is likewise true for the method that, in the case of eye measurements, the reference or measurement beam is influenced, regarding dispersion influences of the eye, by means of a preferably adjustable, dispersion-compensating element.

Since there is a close connection between focusing and the correction of dispersion, it is favorable to couple the adjustment of the focusing element and the setting of the dispersion-correcting element, for example by mechanical or electrical coupling, so as to obtain synchronous adjustment of the dispersion-compensating element and of the focusing element.

Thus, the invention provides an interferometer which measures several partial lengths of the eye at the same time by effecting individual measurements of the separated measurement regions. These separate measurements are preferably carried out simultaneously by corresponding separate superposition of the measurement beam with radiation from different reference beam paths and separate detection of the superimposed radiation. In doing so, separate spectrometers can be used for the separate detections if, as is the case for several variants of the FD OCT, spectrally selective detection is effected.

As already mentioned, the apparatus and method according to the invention are suitable, in particular, for measuring the human eye, while also allowing to examine other partially transparent objects.

By adding to the apparatus a scanning device which deflects the beam transversely over the eye, for example by parallel shifting or beam deflection, e.g. by means of scanning mirrors, it is possible to generate a three-dimensional sample image.

The principle according to the invention allows to effect several partial measurements at the same time, virtually as "one-shot" recordings, or even measurement sequences comprising many individual measurements in quick succession, each of said measurements consisting of several partial measurements.

The apparatus according to the invention is conveniently controlled in operation by a corresponding control device. This control device ensures the aforementioned operation and, in particular, the realization of the aforementioned modes of operation. Advantageously, the control device is also suitably designed, for example as a computer and corresponding program means, to prepare the measurement signal from the electrical signals of the detector(s), in particular the Fourier transformation required for FD OCT.

The invention determines, for at least two spaced-apart sample regions in a transparent and/or diffusive object, i.e. in an eye, the distances of structures in the sample regions within a measurement time in the sub-second range. For this purpose, an arrangement according to a Michelson interferometer is preferably used. Short-coherence radiation is used in the interferometer design. For example, the short-coherence radiation coming from a source of radiation is split into a measurement beam and a reference beam. The radiation used for the measurement beam and the reference beams, thus, has a short coherence length as compared to the distances between the sample regions. The measurement beam irradiates the sample regions. The reference beam is split into at least two spatially separated reference beam paths, which impose different delay variations upon the reference beams guided in said beam paths, said delay variations being pre-tuned to the distance between the sample regions. The reflected reference beams are then separately combined, in an interfering manner, with the reflected and/or back-scattered measurement beam. The combined beams are detected and, as already mentioned, the detected signal is Fourier-evaluated for distance measurement.

In order to measure the distance between the measurement regions of a transparent and/or diffusive sample, as required for distance, length, thickness and profile measurements, the sample is irradiated with a measurement beam, and a reference beam is provided for each sample region. The sample regions may be located at different locations in the direction of incidence of the optical radiation as well as laterally offset relative to each other. The delay difference between the reference beam paths corresponds to an optical distance of the sample regions with respect to the direction of incidence of the measurement beam, wherein at least one of the sample regions reflects and/or back-scatters at least at a low level (typically at least $10^{-4}$% of the radiation intensity). Of course, the beam configuration of the measurement beam can also be moved, in particular periodically, over the sample, so that the sample is scanned transversely to the axis of incidence. Thus, profiles of the sample can be measured. Instead of allowing only one measurement beam to be incident along an optical axis, it is also possible, of course, to allow several measurement beams to be incident adjacent each other at intervals, in order to allow quicker determination of a surface profile.

Using the apparatus and method according to the invention, a sample can be measured in terms of distances or profiles. Application for optically transparent and/or diffusive samples is particularly preferred, because the inner sample structure can then be measured as well. The delay or path length difference of the spatially separated reference beam paths is adjusted by approximation such that it corresponds to the expected distance, a thickness to be determined etc., within a certain tolerance. Using FD OCT, the deviation of the unknown, not yet determined distance from the pre-set value is determined. For example, if the actual length of a human eye is to be measured, it is already known in advance that an optical length of 34 mm plus/minus 4 mm is to be expected. Thus, the path length difference of the reference beam paths is set to 34 mm, and the signal evaluation of the Fourier analysis will determine the variation within the possible range of 8 mm. Of course, it is quite generally convenient for the apparatus or method, if the path length difference between the reference beam paths is adjustable or adjusted during measurement.

The apparatus or method according to the invention allows measurement not only of the eye's length (centrally, peripherally), but also of the anterior chamber depth (centrally, peripherally), the corneal thickness (centrally, peripherally), the tear film thickness (centrally, peripherally), the lens thickness (centrally, peripherally) and the thickness of the vitreous body as well as of corresponding surface profiles (topographies) of the anterior corneal surface, of the posterior corneal surface, of the anterior lens surface, of the posterior lens surface and of the retina. Further, suitable scanning mechanisms allow to determine radiuses of curvature, e.g. of the anterior corneal surface, of the posterior corneal surface, of the anterior lens surface and of the posterior lens surface.

Of course, a sample region may also comprise several partial regions of interest. Thus, a sample region may be defined such that it comprises the entire anterior chamber of the eye. For this purpose, the measurement beam is focused on a location between the anterior corneal surface and the posterior lens surface. This enables detection of the reflection at the anterior corneal surface, the posterior corneal surface, the anterior lens surface and the posterior lens surface within a sample region. The distance between the posterior corneal surface and the anterior lens surface is then the anterior chamber depth. The only prerequisite for this is that the measurement region in the sample region should be sufficiently large to cover a region from the anterior corneal surface to the posterior lens surface.

Further, the inventors have found that, for specific types of spectral analysis properties, Fourier domain short-coherence interferometry is capable of detecting the entire length of the human eye in one measurement, if certain parameters are complied with by the spectrometer. The pixel number or the number of sensitive cells of the detector array has turned out to be an essential parameter. Therefore, a further invention provides an embodiment of the initially mentioned apparatus, wherein a spectrometer arrangement detects the superimposed beams, said arrangement comprising an element which spectrally spreads the beams and a detector array which comprises at least 7,000 individual photo-sensitive cells. The measurement range achieved by such a detector array is so large, for example at a wavelength of between 700 and 900 nm as well as a spectral bandwidth of 10-30 nm of the radiation used, that the full eye length can be measured thereby. Therefore, in an analogous manner, the initially mentioned method also provides for the use of a spectrometer arrangement for detection of the superimposed beams, which arrangement comprises an element that spectrally spreads the beams and a detector array comprising at least 7,000 individual photo-sensitive cells.

Any method steps mentioned in the preceding or following specification, in particular signal evaluations, control of adjustable components, such as e.g. a wavelength-sweepable source of radiation, etc., can be performed by the control unit in the apparatuses according to the invention, said control unit comprising suitable utilities, for example software control, for this purpose. Of course, the features described herein can also be realized in combinations other than those described. In particular, a specific feature can also be used without other features described together with it.

The measurement signal of short-coherence interferometry, which (with analogy to the corresponding ultrasound method) is the so-called A-scan signal, is the cross-correlation of the reference light with the object light at the interferometer output. By Fourier transformation of a spectral intensity distribution, the autocorrelation of the underlying light signal is obtained. Forming the Fourier transformation (FT) of the light spectrum I(k) at the interferometer output yields an autocorrelation of the sums of the superimposed reference and object waves. This autocorrelation also contains the desired cross-correlation of the interferogram IN(z) of the reference light with the object light. IN(z) is the A-scan signal, which is displayed, for example, on a computer monitor. The signal peaks mark the positions of light-reflecting locations in the measurement object, as shown in FIG. 21. Therefore, the A-scan signal can be simply written as follows:

$$IN(z) \sim FT\{I(k)\},$$

wherein k is the wave number, for which the following is known to apply: $k=\pi/\lambda$. z is the coordinate in the local region; IN(z) is the interferogram and I(k) is the intensity spectrum of the light used. In short-coherence interferometry according to the prior art, light of super-luminescence diodes in the near-infrared region with wavelength bandwidths of around $\Delta\lambda=20$ mm is used in most cases. This results in a coherence length and, thus, an accuracy of measurement on the order of magnitude of 30 μm. The direct use of FD OCT for eye length measurement was unsuccessful because the previously available photodiode arrays did not allow to detect the entire spectrum corresponding to the eye length. The field depth T (previously referred to also as Z), which a detector array provides, is obtained from $$T = N \cdot \pi / (2\Delta k),$$

wherein N is the pixel number or diode number of the photodiode array and $\Delta k$ is the wave number bandwidth of the light. Using arrangements that are common nowadays, field depths of approximately $T \approx 5$ mm are achieved. Obviously, distances greater than T can not be measured, as is readily apparent from FIG. 21.

Measurement of the entire eye length requires measurement fields having a depth of 40 mm and in some cases even greater measurement fields. This problem is avoided, for example, by EP 1 602 320 A1 using an interferometer which—like the aforementioned IOL Master of Carl Zeiss Meditec AG—uses the cornea as reference surface and reduces the reference beam/measurement beam path difference by means of a flexible optical extension in the beam path. Thus, the depth of the measurement window only has to cover the differences between the length of the eye and path difference of the reference beam and measurement beam. However, this principle is also disadvantageous because the spectrum used for measurement at the interferometer output is based on an interferogram of two light waves, both formed by reflection at biological boundaries (for example, the anterior corneal surface and the anterior eye lens surface). A signal is visible only if both of the very unstable signals are present at the same time. This is not always easy to realize; in addition, it is not easy to obtain maximum sensitivity by optimization of the intensities of these two waves, because the reflectivities of both biological boundaries, which are the reflectivities effective for measurement, also depend on the beam position which is difficult to control due to inherent movements of living objects. Finally, the sensitivity of FD OCT depends on the position of the signal in the measurement field. Therefore, detection with optimum sensitivity is not possible for both signals that define a distance to be measured.

The present Fourier domain interferometry (FD OCT) for measurement of partial lengths of the eye preferably uses two measurement fields at the same time, with a separate respective reference and measurement beam in each case. In doing so, the eye is illuminated by a double measurement beam consisting of two axially offset individual beams, and two reference beams are used.

In this "method of two measurement fields" the measurement positions of two measurement fields become freely selectable to large extents by the use of the respective reference mirrors, and at the same time, two separate partial lengths having the extent of the measurement field can be visualized from the reflections contained in the fields. It will be useful to select the reference beam lengths such that signal peaks (S1 and S2) contained in the two measurement fields do not overlap in the result of measurement, i.e. in the Fourier transform of the spectrum, but are displayed separately, as illustrated in FIG. 22. Now, the distance between the two signal peaks, however, no longer corresponds to the actual distance between the underlying reflecting surfaces, but is shortened by the difference between the two reference beams. It is possible to follow the positions of the measurement surfaces in real time and to determine whether a useful measurement is being carried out. An identification of the measurement signals is also easily possible due to the coupling of their positions to the corresponding reference mirror. In the known approach, the useful field depth T or Z is also limited by the fact that the short-coherence interferogram IN(z) is calculated on the basis of the real intensity I(k) registered by the detector array, and not on the basis of the (complex) frequency spectrum $\hat{I}(k)$ of the light at the interferometer output. This results in a Hermitian function: one does not obtain the interferogram IN(z), but the autocorrelation of the sum of the superimposed reference and object waves and, if the reference mirror is optimally positioned, two separate reconstructions of the measurement signal, which are symmetrical to the coordinate origin, namely one reconstruction at positive coordinates and one at negative coordinates, which divides the measurement depth at least by two. Two solutions are given for this problem here:

1) The complex spectrum $\hat{I}(k)$ can be mathematically obtained a posteriori, i.e. following the actual measurement, by mathematically complex correlating of the measured real intensity I(k) with the respective quadrature component or "blind component". This causes the reconstruction of the measurement signal to disappear in the case of negative coordinates:

$$\hat{I}(k) = \frac{1}{2}[I(k) + i \cdot \mathrm{HT}\{I(k)\}] \quad (1)$$

wherein HT {I} is the Hilbert transform of I or the quadrature component assigned to I.

2) The quadrature component assigned to the real intensity I(k) can also be measured experimentally by introducing a phase offset of 90° in the spectrum I(k). The technical solution is now based on small shifts of the diffraction grating used in the spectrometer. Basically, the field depth of FD OCT can be doubled by both solutions and one measurement field is sufficient for lower field-depth requirements. However, it should be noted that FD OCT has a depth-dependent sensitivity. Thus, sensitivity is at a maximum for the boundary of a distance which is closest to the virtual reference mirror position. However, said sensitivity can be more than 10 dB less for the boundary, which is maximally distant therefrom, which may prevent a valid measurement. Further, the A-scan signal computed by the complex spectrum still includes interfering terms. The invention also resolves this problem, because each boundary of a distance to be measured can be detected with maximum sensitivity by a corresponding reference beam length in the respective measurement field.

The measurements yield a signal peak for each light-reflecting location in the eye by Fourier transformation of the spectrum. Assigning these signals to the actual eye structures is not always easy. Especially the signals of the retina can be very complex, as shown, for example, in FIG. 23. In this case, the light reflected at the retinal pigment epithelium (RPE) usually prevails. The distance of this signal from the anterior corneal signal would be suitable for eye length measurement. However, depending on the position of the eye, other signal peaks of the retinal signal complex also prevail sometimes, which may lead to incorrect measurements. There are the following three possibilities to obtain unambiguous length measurements:

1) Several measurements can be carried out, because FD OCT is very quick. Experience shows that, in most cases, this will also yield signals having a strong RPE peak, which can be recognized because of the fact that it appears at the greatest z positions of the retina signal complex.

2) The signals of several measurements can be added up; this will yield a sum with a prevailing RPE peak.

3) The fact can be used that the light remitted by the RPE has a different polarization than light from the other retinal layers. Therefore, a reference beam which is polarized orthogonally to the illuminating light can more strongly suppress the light reflected by the other retinal layers than that from the RPE.

If the eye is illuminated, as also provided herein to some extent, by a double beam, the components of this double beam will be reflected back at all interfaces of the eye. This leads to reflected waves whose path differences are reduced considerably if the initial path difference is not greater than twice the eye length plus the field depth. Such waves yield a spectrum which is rich in contrast. In order to avoid artifacts generated thereby, the initial path difference of the components of the illuminating double beam should preferably be greater than twice the eye length plus the field depth.

The invention will be explained in more detail below, by way of example and with reference to the drawing, wherein:

FIG. 4 shows a schematic representation illustrating the effect of a diffraction grating of the interferometer according to FIGS. 1 to 3;

Figure 1:
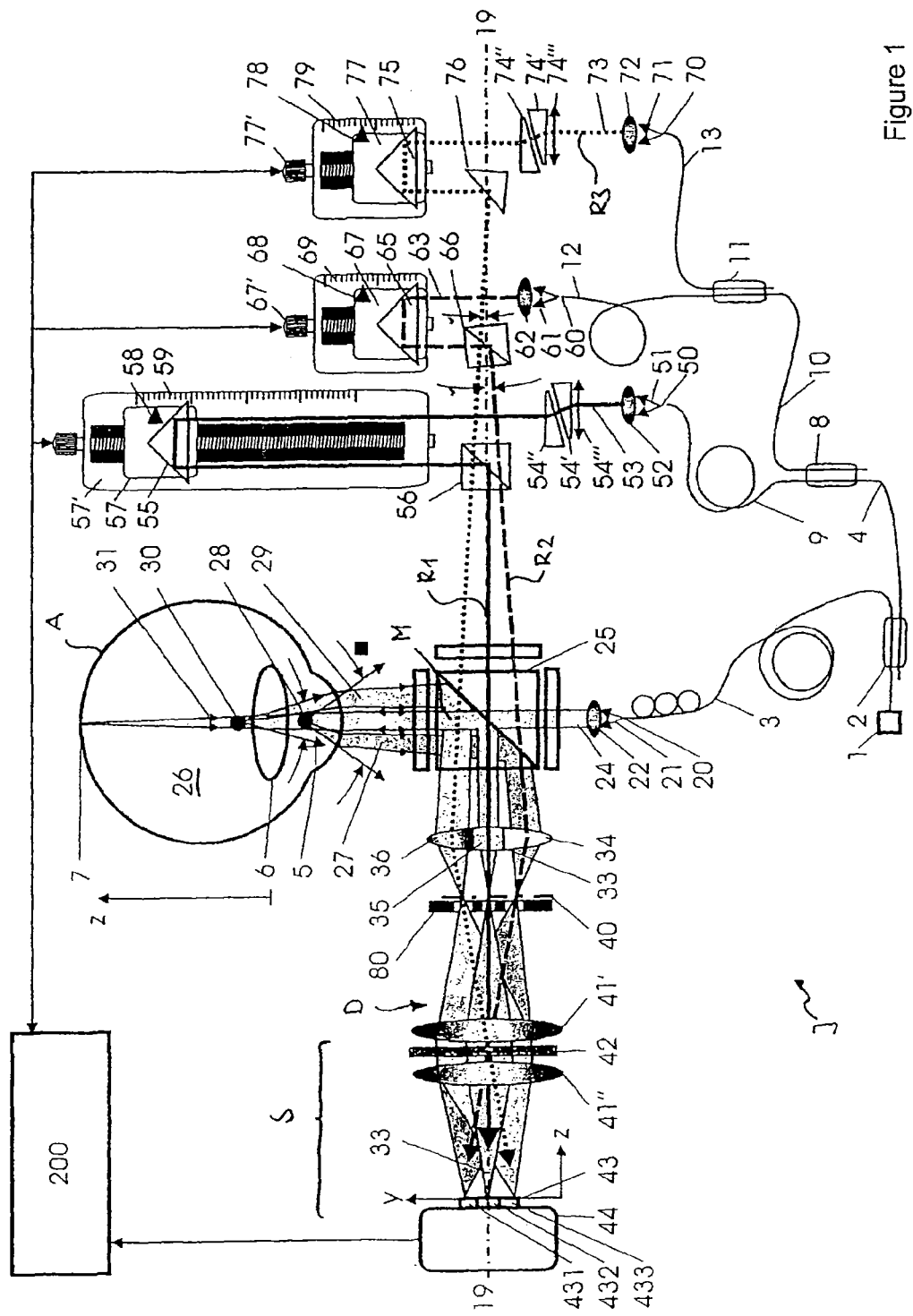
FIG. 1 shows an interferometric apparatus for measurement of an eye, wherein measurement radiation is made to interfere in a spatially separated manner with radiation from three reference beam paths.
Figure 2:
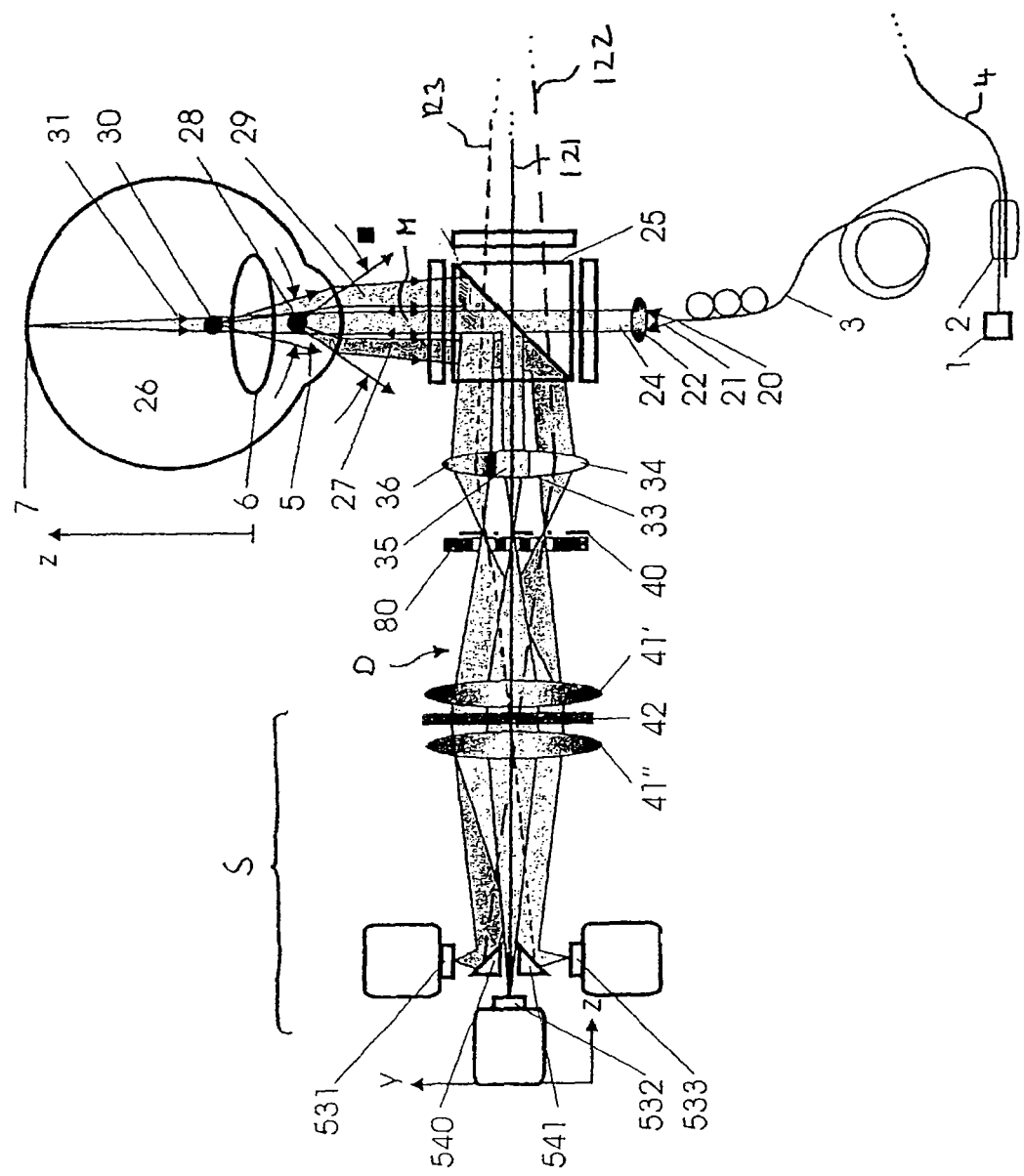
FIG. 2 shows a representation similar to that of FIG. 1 with a modified spectrometer unit.
Figure 3:
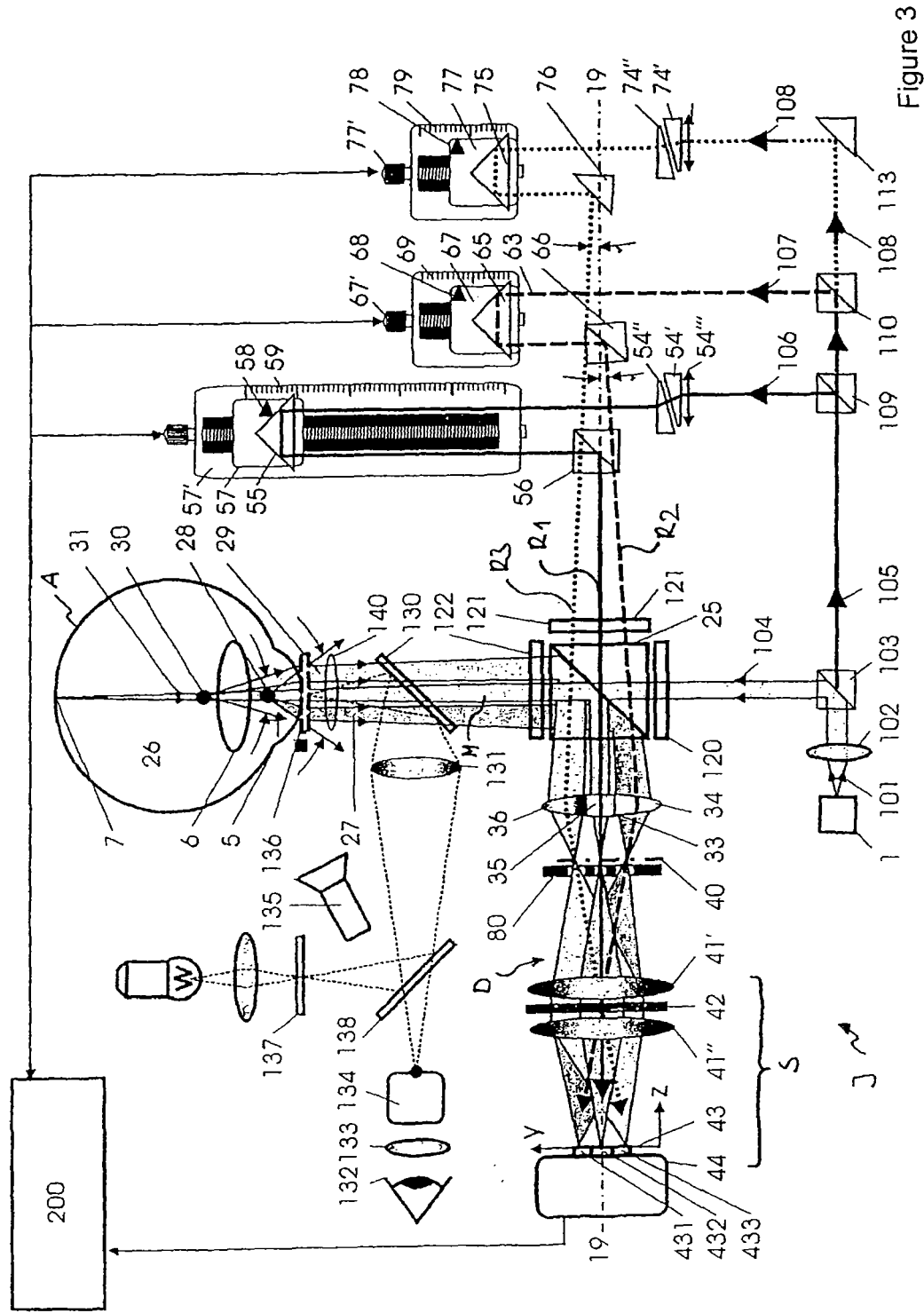
FIG. 3 shows a representation similar to FIG. 1, but now using bulk optics instead of light guide fibers.
Figure 6:
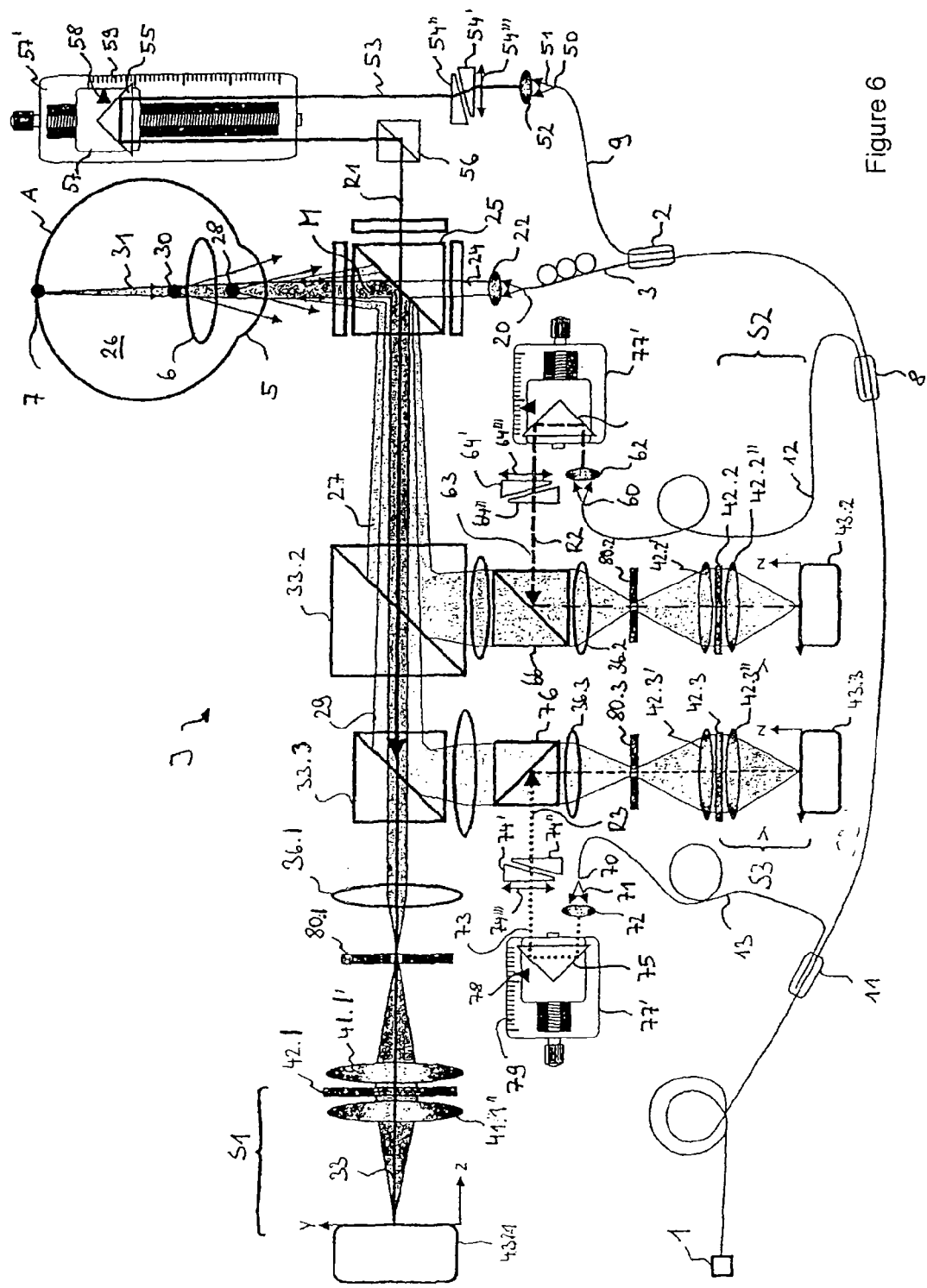
Figure 9:
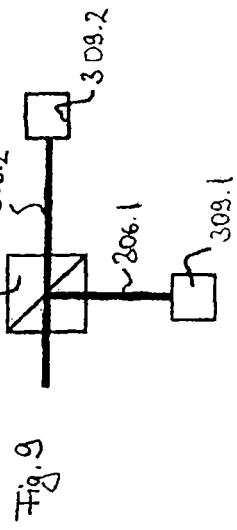
Figure 8:
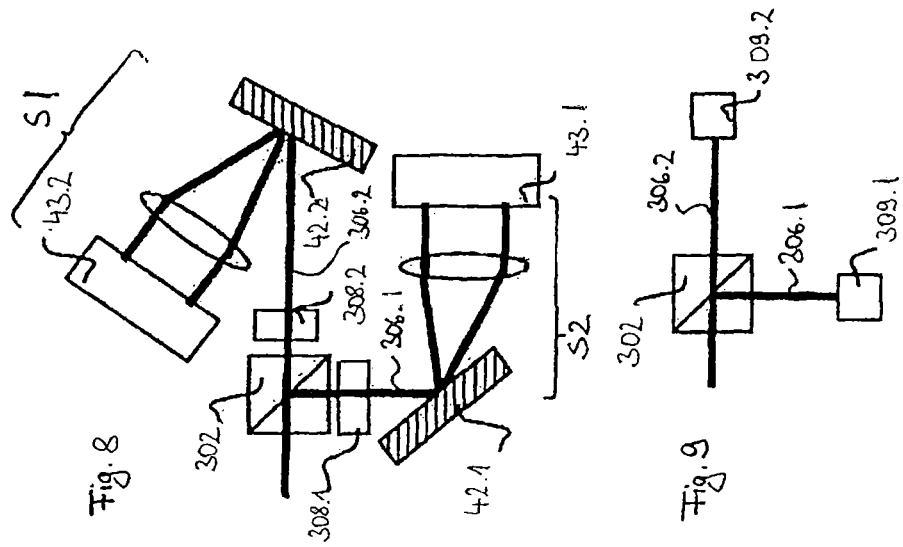
Figure 7:
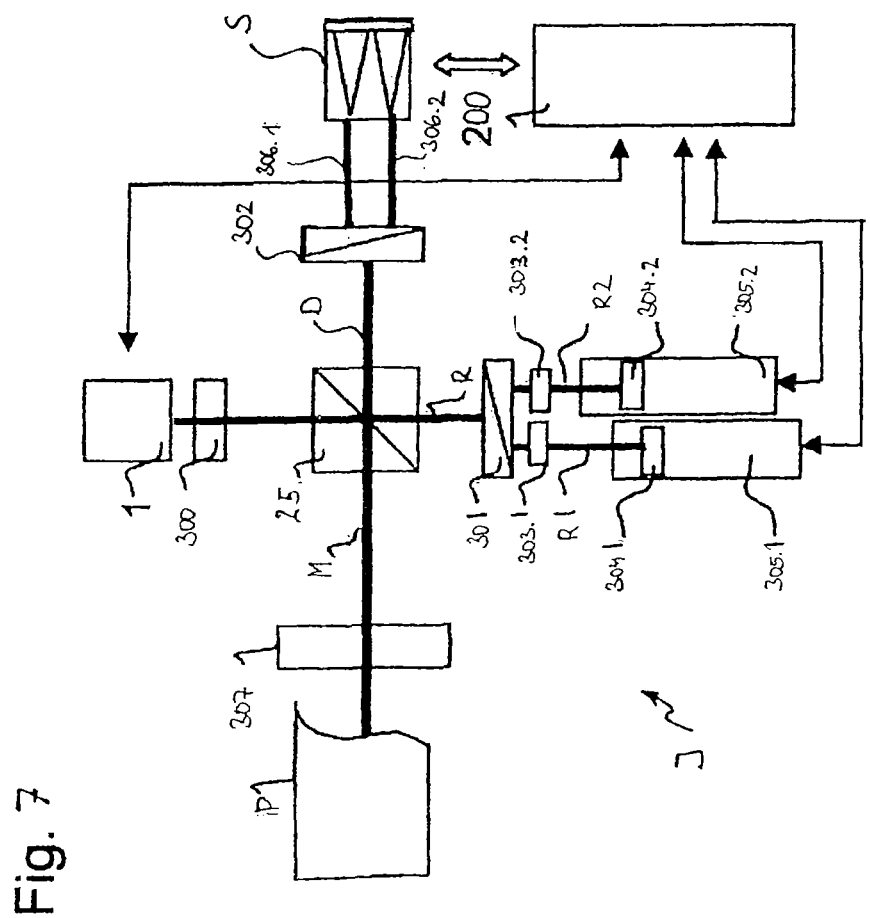
Figure 18:
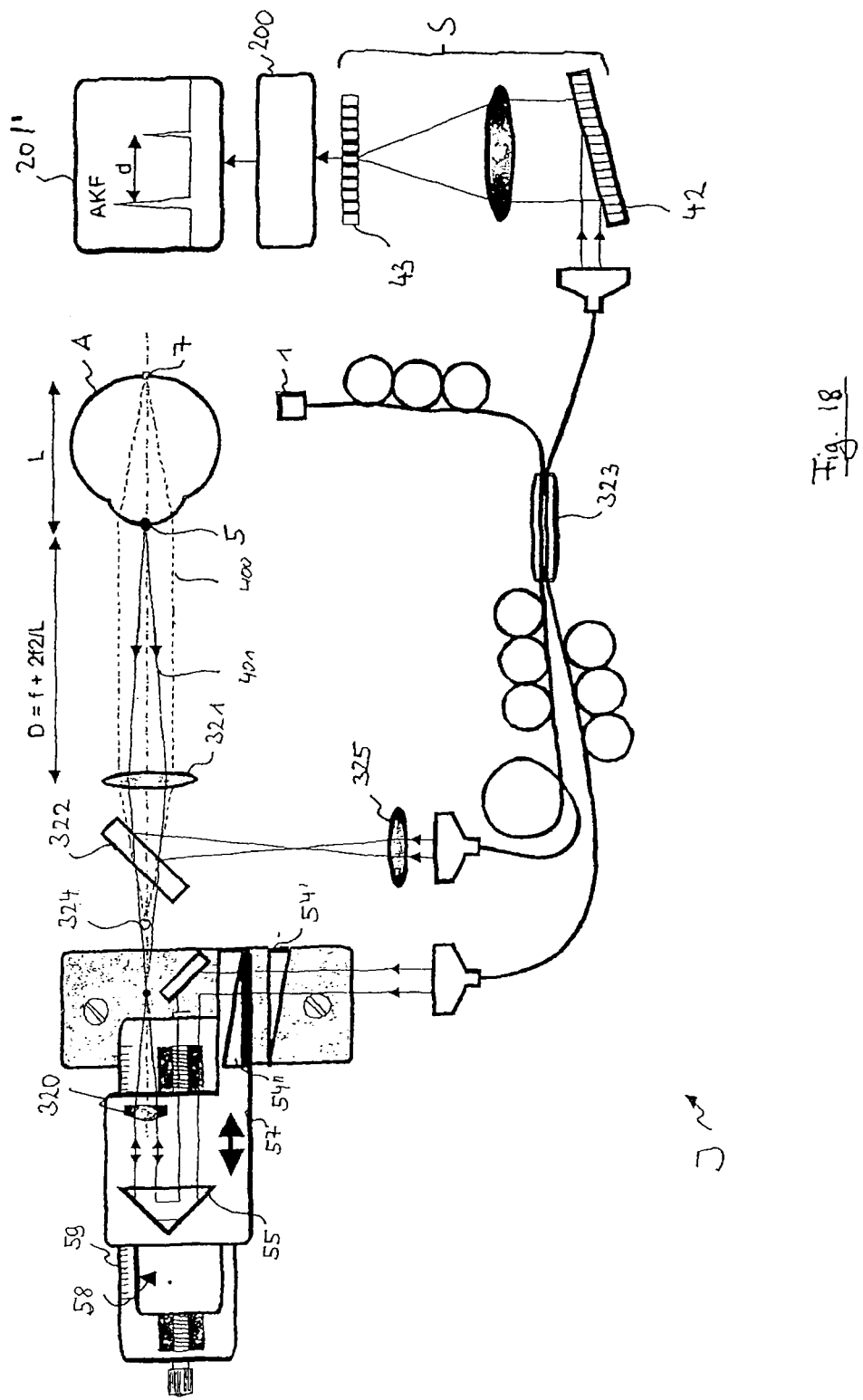
Figure 21:
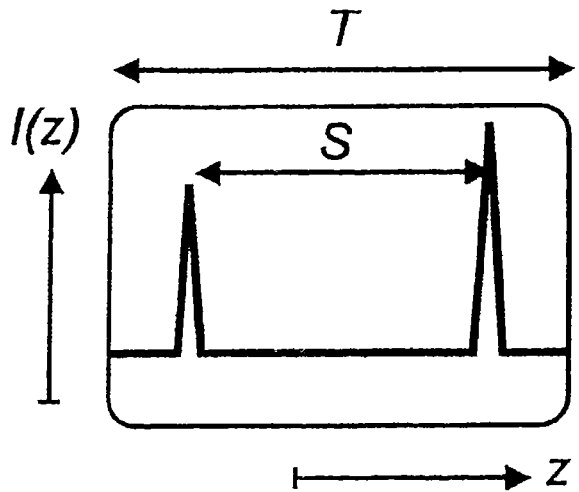
Figure 22:
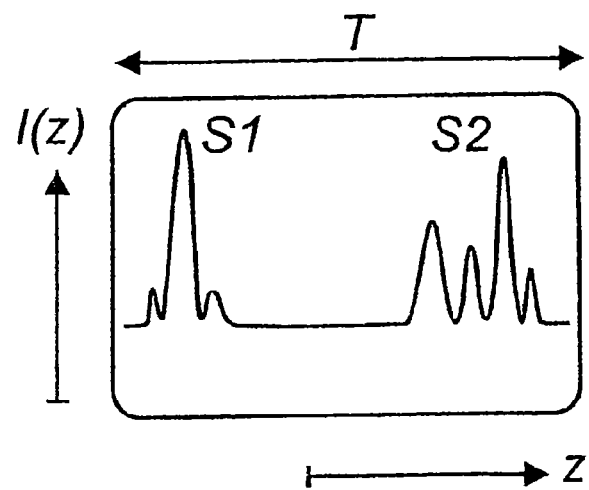
Figure 23:
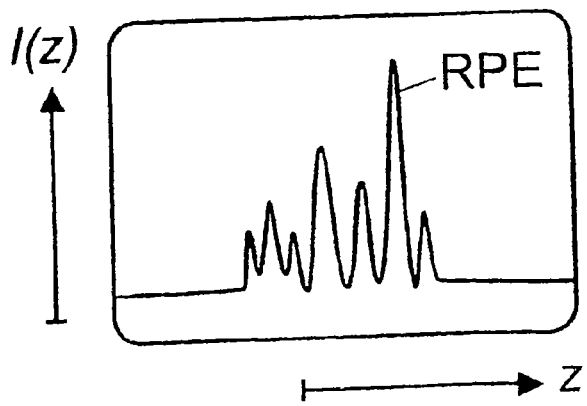
Figure 24:
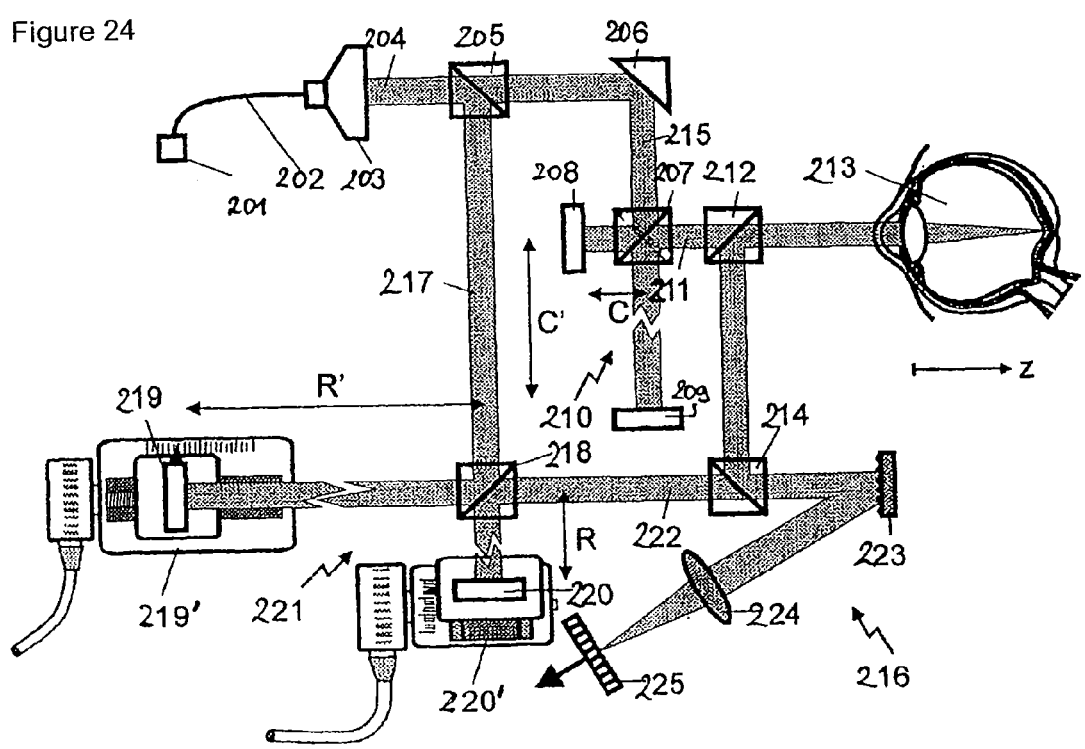
Figure 25:
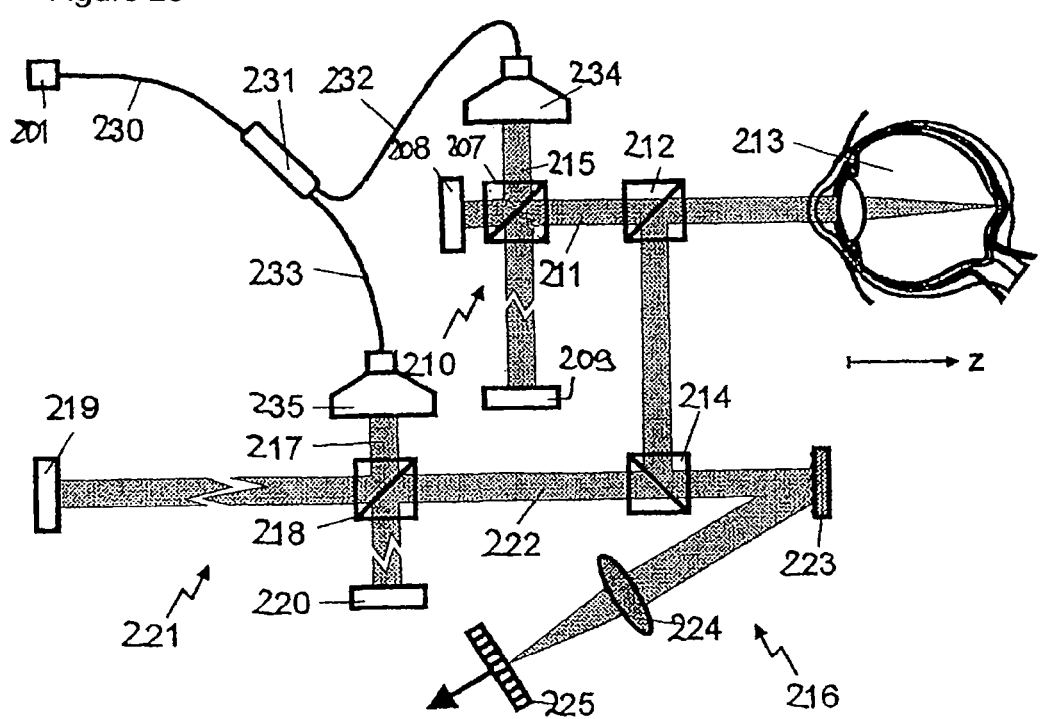
Figure 26:
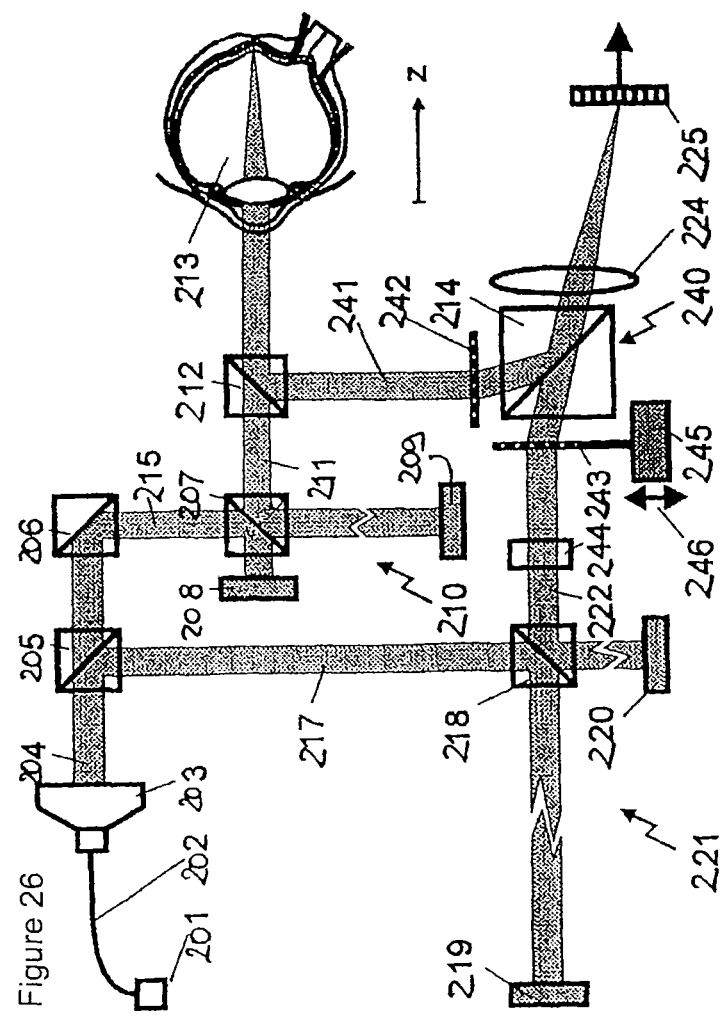
Figure 27:
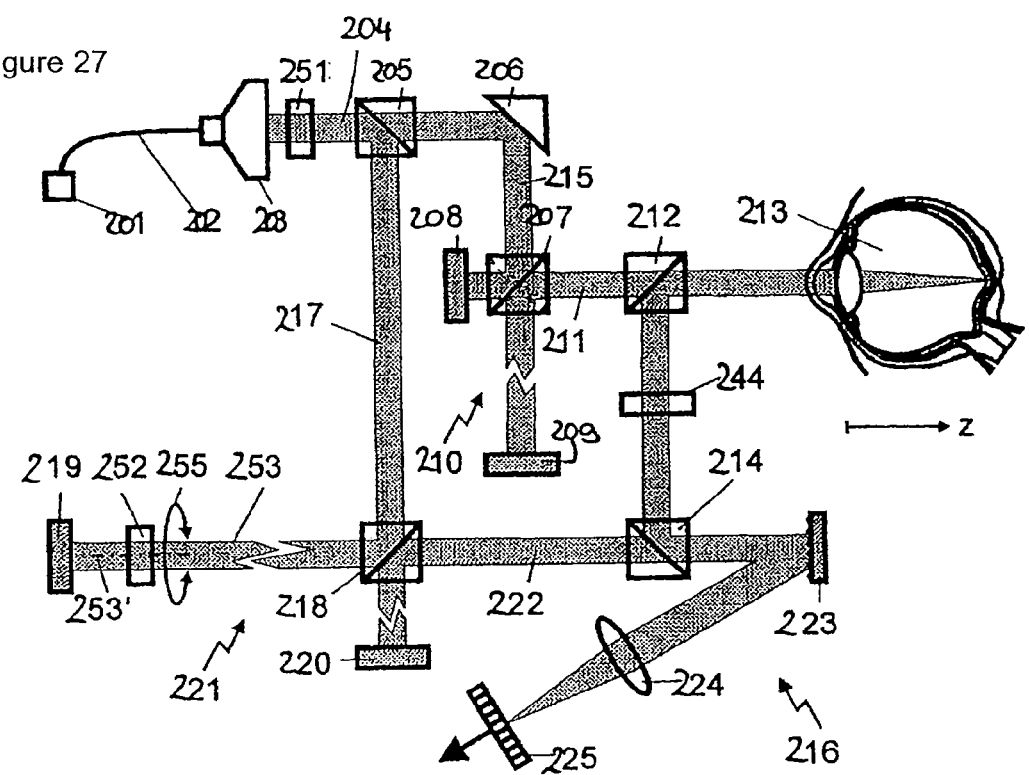
Figure 28:
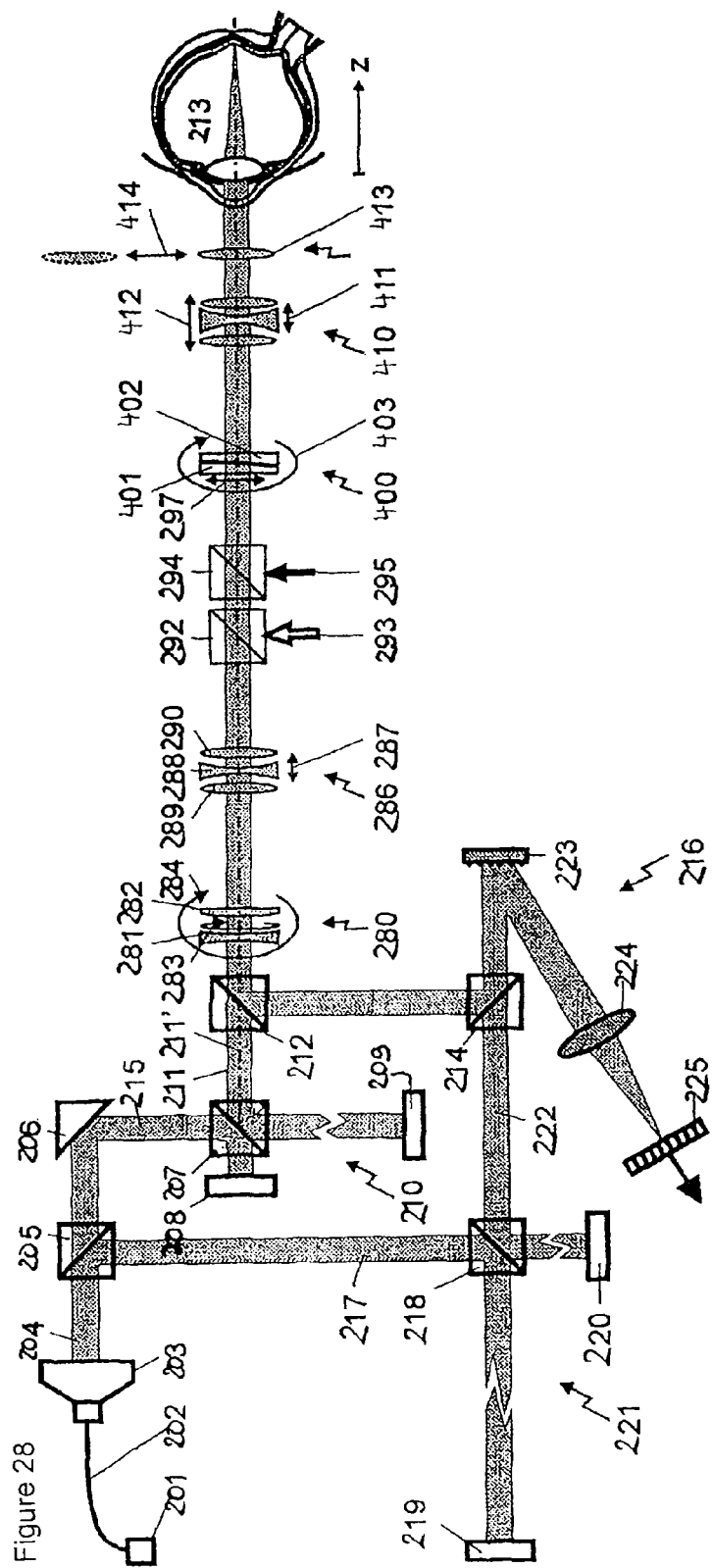

FIGS. 5a-c show exemplary embodiments of optics comprising a partitioned pupil, such as those which can be used in the interferometers of FIGS. 1-3;

FIG. 6 shows a further interferometer similar to that of FIG. 1, but having a different spatial separation of the superposition of the measurement beam and the reference beams;

FIG. 7 shows an interferometer similar to that of FIG. 1, wherein the separate superposition of the measurement beam and the reference beams is effected by polarization separation;

FIGS. 8 and 9 show details of a possible construction of the interferometer of FIG. 7;

FIG. 10 shows an interferometer similar to that of FIG. 10, in which separation is effected spectrally;

FIG. 11 shows a graphic representation explaining the effect of spectral separation;

FIGS. 12 and 13 show detailed views of components of the type which can be used in the interferometer of FIG. 10;

FIG. 14 shows an interferometer similar to that of FIG. 7, wherein individual superposition of the measurement beam and of the reference beams is effected sequentially;

FIG. 15 shows an interferometer similar to that of FIG. 7, wherein a double beam is used as the measurement beam;

FIG. 16 shows a modification of the interferometer of FIG. 15, comprising only a single spectrometer;

FIG. 17 shows a spectrometer similar to that of FIG. 15, but without polarization separation, using a double beam instead;

FIG. 18 shows a fiber-optical construction for the spectrometer of FIG. 17;

FIG. 19 shows a simplified interferometer for simultaneous detection of regions which are spaced apart in depth;

FIG. 20 shows a simplified short-coherence Fourier domain interferometer for measurement of two or more regions which are spaced apart in depth;

FIG. 21 shows a simplified measurement signal profile for a depth measurement (A-scan);

FIG. 22 shows a simplified measurement signal profile for a depth measurement using a more complex signal;

FIG. 23 shows a measurement signal profile for measurement of the retina;

FIG. 24 shows an apparatus for short-coherence interferometry using a double measurement beam and a double reference beam;

FIG. 25 shows a further apparatus for short-coherence interferometry using a double measurement beam and a double reference beam;

FIG. 26 shows a further apparatus for short-coherence interferometry using a double measurement beam and a double reference beam;

FIG. 27 shows a further apparatus for short-coherence interferometry using a double measurement beam and a double reference beam, and FIG. 28 shows a further apparatus for short-coherence interferometry using a double measurement beam and a double reference beam, in which different, quite generally possible auxiliary units are present by way of example.

FIG. 1 shows a fiber-optic implementation of an interferometer I. The remitted reflection radiation is simultaneously registered in a Michelson set-up comprising several pupil-separated beam paths separated and respective reference beams for different eye structures. For this purpose, fiber-optical couplers are used; use can also be made of other fiber-optical or open-beam interferometer structures, for example using fiber-optical circulators. Moreover, the simultaneous measurement is effected at three positions of the eye's structure (anterior corneal surface, anterior lens surface and fundus). The interferometer can also be modified for measurement at more or less than three positions. For the sake of simplicity, the drawings show only the beam axes in many cases. Also, the term "beam" is sometimes used below for the sake of simplicity, instead of "ray bundle" or "pencil of rays".

Light coming from a short-coherence light source 1, for example a super-luminescence diode equipped with a "pig-tail" fiber, or from any other short-coherence light source is split by a fiber coupler 2 into an interferometer measurement arm 3 and an interferometer reference arm 4. For detection of three structures located in different depth regions z of the eye, namely the cornea 5, the eye lens 6 and the eye fundus 7, by a Fourier domain short-coherence interferometer, three reference beam paths R1, R2, R3 with corresponding ray bundles are used simultaneously. These beam paths are split off from the reference arm fiber 4 via fiber couplers: one coupler 8 splits a fundus reference beam path R1 off into a fiber 9. The remaining radiation in a fiber 10 is split by a coupler 11 into a fiber 12 for the corneal reference beam path R2 and a fiber 13 for the eye lens reference beam path R3. The fiber lengths for these three reference beam paths are dimensioned such that, despite the short coherence length, interference with the respective ray bundles coming from the different object depths, namely the cornea 5, the eye lens 6 and the eye fundus 7, occurs at a photodetector array 43.

The illumination radiation 21 exiting the fiber 3 at the output point 20 is collimated by optics 22, for example a fiber collimator, passes through a beam splitter 25 as a parallel illumination ray bundle 24 and illuminates the eye 26. A cornea reflection beam 27 reflected by the anterior surface of the cornea 5 has its virtual origin in a $1^{st}$. Purkinje-Sanson image 28 and an eye lens reflection ray bundle 29 reflected by the anterior lens surface has its virtual origin in a $3^{rd}$ Purkinje-Sanson image 30. Both of these reflection ray bundles diverge at different angles. For the sake of clarity, FIG. 1 only shows a reduced angular range. A further reflection comes from the fundus 7 and forms the reflected fundus reflection ray bundle 31.

The reflection ray bundles 27, 29 and 31 reflected at the eye are, thus, present as a superimposed measurement beam M and are directed by the beam splitter 25 into a detection branch D and, there, onto relay optics 33 feeding a spectrometer S. The relay optics 33 trims the measurement beam M, which is a mixture of the three reflection ray bundles, for the subsequent spectrometer S. In the example of FIG. 1, these optics consist of three optical parts 34, 35 and 36 having different focal lengths. The focal lengths are designed such that the three reflection ray bundles, which are contained in the measurement beam M and have been reflected at the eye from different depths, are focused in the same image plane 40 in front of the spectrometer S; the foci are imaged by the spectrometer optics 41' and 41" via a diffraction grating 42 onto a photodetector array 43, for example an array camera 44. The spectrometer optics 41' and 41" can also be combined into one single optical system preceding or following the diffraction grating 42.

As shown in FIG. 4, the diffraction grating 42 disperses the various wavelengths of the incident light in the x direction onto photodetectors 435 of the photodetector array 43. In FIG. 4, 140 is a light bundle of the zeroth order of diffraction of the grating 42, said light bundle being focused by the optics 41' and 41" (cf. FIG. 1); 141 and 142 are light bundles of first orders of diffraction at different wavelengths, which light bundles are dispersed by the diffraction grating in the x direction and are focused by optics 41' and 41" on the photoreceivers of the array at a column 432. The light bundles of the first order of diffraction have superimposed upon them spectral components of the reflection ray bundle 31 remitted by the fundus 7 with the corresponding spectral components of the associated reference beam 53 from the reference beam path R1. The reflection ray bundles 27 and 29 remitted by the cornea 5 and the eye lens 6 and also having superimposed upon them reference light from the reference beam paths R2 or R3, respectively, are focused by the optics 41' and 41" at adjacent array columns 431 and 433.

In the first reference beam path R1, the ray bundle 51 exiting the fiber 9 at the output point 50 is collimated by optics 52 of a fiber collimator, passes as a parallel reference beam 53 through two dispersion-compensating prisms 54' and 54" and is reflected by a reflection prism 55 via a beam splitter 56 into the interferometer I along an optical axis 19 of the reference arm 4. The reference beam 53 is represented here only by its main ray. Further, FIG. 1 shows that, on the photodetector array 43, this first reference beam 53 has superimposed upon it the reflection ray bundle 31 coming from the fundus 7. By adapting the optical length of the first reference beam path R1, which extends from the coupler 2 to the beam splitter 25, to the optical length from the coupler 2 via the fundus 7 of the eye A and back to the beam splitter 25, interferences of the overlapping ray bundles are ensured; this means that the origin of the corresponding measurement field is located at the fundus 7. This is set by suitably selecting the fiber lengths and/or the position of the reflection prism 55. For this purpose, an adjusting mechanism is preferably provided.

Said mechanism may be designed, for example, as shown in FIG. 1. The reflection prism 55 is mounted to a table 57 of a manually or electrically operable shifting unit 57'. Adaptation to different eye lengths and eye positions can further be effected during a measurement sequence by a manually or electronically driven shift of the reflection prism 55 using the shifting unit 57'. The actual position of the prism 55 can be determined with the help of a pointer 58 and of a scale 59. Alternatively, electronic position indicators can also be used and their data can be input directly to the computer 200. For compensation of the subject-dependent dispersion of the eye, the prisms 54' and 54" can be shifted relative to each other in the direction of the double arrow 54'''.

In the second reference beam path R2, the ray bundle 61 exiting the fiber 12 at the output point 60 is collimated by optics 62 of a fiber collimator and is reflected 63 into the beam splitter 25 by a reflection prism 65 and via a beam splitter 66 as a parallel reference beam, at an angle $\beta$ to the optical axis 19 of the reference arm 4. FIG. 1 shows that, at the photodetector array 43, the second reference beam 63 has superimposed upon it the reflection ray bundle 27 coming from the cornea 5. By adapting the optical length of the second reference beam path R2, which extends from the coupler 2 to the beam splitter 25, to the optical length from the coupler 2 via the cornea to the beam splitter 25, short-coherence interferences of these two superimposed light bundles are ensured, or the origin of the measurement field is defined, respectively. However, this can also be effected here by suitable selection of the fiber length and/or the position of the reflection prism 65. In this case, too, an adaptation to different eye lengths and eye positions can preferably be effected during measurement, namely by shifting the reflection prism 65 by means of a manually or electrically operated shifting unit 67'. The position of the prism 65 can be determined with the help of a pointer 68 and of a scale 69. Alternatively, electronic position indicators can also be used here and their data can be input directly to the computer 200.

In the third reference beam path R3, the ray bundle 71 exiting the fiber 13 at the output point 70 is collimated by optics 72 of a fiber collimator and is reflected, after reflection at a reflection prism 75, by a reflection prism 76 into the interferometer I as a parallel reference beam 73, at an angle $\alpha$ to the optical axis 19 of the reference arm 4. FIG. 1 shows that, at the photodetector array 43, the third reference beam 73 has superimposed upon it the reflection ray bundle 29 coming from the anterior surface of the eye lens 6 or from the $3^{rd}$ Purkinje-Sanson image 30. By adapting the optical length of the third reference beam path R3, which extends from the coupler 2 to the beam splitter 25, to the optical length from the coupler 2 via the anterior surface of the eye lens to the beam splitter 25, short-coherence interferences of the combined light bundles are ensured, or the positions of origin of this measurement field are defined, respectively. This is also effected here by suitable selection of the fiber length and/or the position of the reflection prism 75. Also, during a sequence of eye measurements, an adaptation to different eye lengths and eye positions can be preferably effected, namely by shifting the reflection prism 75 by means of a manually or electrically operated shifting unit 77'. The position of the reflection prism 75 can also be determined here with the help of a pointer 78 and of a scale 79. Alternatively, electronic position indicators can also be used here and their data can be input directly to the computer 200.

FIG. 3 shows an interferometer I, which substantially corresponds to the interferometer of FIG. 1, so that the same reference numerals are assigned to the same elements. In contrast to FIG. 1, the interferometer, however, has a free-beam optical design here. An initial ray bundle 101 emitted by the short-coherence light source 1 is collimated by optics 102 and is incident as a parallel beam on a beam splitter 103. The beam splitter 103 divides the ray bundle 101 into a measurement ray bundle 104 in the interferometer measurement arm 3 and a ray bundle 105 in the interferometer reference arm 4. Again, the ray bundle 105 is represented by its main ray here.

The illumination ray bundle 104 reflected by the beam splitter 103 passes through the beam splitter 25 and illuminates the eye 26. A measurement beam M returns, which again contains a mixture of the following reflection ray bundles: the reflection ray bundle 27 reflected at the anterior corneal surface has its virtual origin in the $1^{st}$ Purkinje-Sanson image 28, and the eye lens reflection ray bundle 29 reflected by the anterior lens surface has its virtual origin in the $3^{rd}$ Purkinje-Sanson image 39. These two reflection ray bundles are divergently reflected and expand correspondingly. Again, FIG. 3 only shows a reduced angular range of these two reflection ray bundles. A further reflection comes from the fundus 7 and forms the fundus reflection ray bundle

31. Insofar, the same conditions are present as in the interferometer I of FIG. 1. This also applies to the detection of the superimposed beams in the detection branch D.

As in the fiber-optical interferometer I of FIG. 1, three reference beam paths R1, R2, R3 are used for the three structures located in different depth regions of the eye, for example the cornea 5, the eye lens 6 and the fundus 7. These reference beam paths are generated here with the help of beam splitters 109 and 110. In other respects, coupling-in and path length adjustment remain unchanged.

In the interferometer I of FIG. 3, an observation apparatus consisting of a partially transmitting mirror 130 and of optics 131 is additionally provided for observation of the position of the subject's eye 26 relative to the fundus reflection ray bundle 31. Observation of the subject's eye can then be effected directly (132), with the help of an eyepiece 133 or with the help of a camera 134. It may also be appropriate to illuminate the subject's eye 26 additionally with an incoherent light source 135. Further, for precise positioning of the subject's eye, an image 136 of a reticle 137 can be used, which is projected onto the cornea 5 via partially transmitting mirrors 138 and 130.

In the case of an eyesight defect, collimating or scattering auxiliary optics 140, which compensate for the eyesight defect, can be placed in front of the eye.

It should also be mentioned that, in order to avoid interfering reflections and to optimize the beam intensities, the illumination ray bundle 104 impinging on the beam splitter 25 can be linearly polarized by means of a polarizer 120, and the beam splitter 125 can be designed as a polarizing beam splitter. Using further optical polarization components, such as $\lambda/4$ plates in positions 121 and 122, reflection losses of the reference and reflection ray bundles during several passes through the beam splitter can be largely avoided, as it is known in the art. Such methods known in optical engineering can also be used for the beam splitters 56 and 66.

The above-described observation apparatus, consisting of the partially transmitting mirror 130 and the optics 131 as well as the auxiliary optics 140 for compensation of ametropias of the subject's eye can also be used into the interferometer I of FIG. 1. Also, in order to avoid interfering reflections and to optimize the beam intensities, the measurement ray bundle 24 impinging upon the beam splitter 25 can also be linearly polarized here by means of the polarizer 120, the beam splitter 25 can be provided as a polarizing beam splitter, and $\lambda/4$ plates can be arranged in positions 121 and 122.

The relay optics 33 can be structured, in the simplest case, using three spherical partial optics 131, 132 and 133 having different refractive powers, as indicated in FIG. 5a. 131', 132' and 133' are the points of passage of the respective optical axes. The partial optics are to be arranged such that their optical axes are located in the y-z plane, corresponding to the spreading of the reference beams in the y-z plane. Alternatively, these three partial optics can also be composed of parts of larger spherical lenses having different refractive powers in order to increase the transmission coefficient of the partial optics, as schematically shown in FIG. 5b. Here, the partial optics 141, 142 and 143 correspond to the optics 131, 132 and 133 of FIG. 5a; the points of passage of the optical axes 141' and 143' can also be located outside the respective partial optics here. Finally, the three partial optics can also be composed of central sections of larger spherical lenses differing in refractive power, as depicted in FIG. 5c. Here, the optics 151, 152 and 153 are provided as central sections of larger optics (as indicated by the circle 151" for 151). 151', 152' and 153' are the positions of the points of passage of the respective optical axes.

Basically, the partial optics of the relay optics 33 can also be positioned at different z positions of the optical interferometer axis 19. It is then only required to ensure by suitable selection of their focal lengths that, in front of the spectrometer, the three reflection ray bundles 27, 29 and 31 are focused in a common plane 40.

The Fourier domain short-coherence interferometer I has to be calibrated due to the separate reflection beams. The result of measurement provided by Fourier domain short-coherence interferometry is the optical distance of the object measurement location relative to the "zero path difference position" (at which the optical length of the measurement beam equals that of the reference beam). Therefore, the distances of the origins of the mutually independent reflection beam paths guiding the reference beams R1, R2, R3 have to be defined. Moreover, the measurement region is limited in depth, for example to approximately 5.3 mm for the initially assumed parameters; therefore, the interferometer I also has to be coarsely pre-adjusted to the expected eye distances. For a basic setting for adaptation and calibration, a planar mirror can be positioned, for example, as an object in the measurement beam path at the expected position of the cornea. Next, all reflection prisms (55, 65 and 75) are positioned such that all associated reference beams 53, 63, 73 show short-coherence interferences with the light bundle reflected by said planar plate. Starting from this basic setting, for example, the positions of one reference mirror each at the expected positions of the anterior lens surface 6 and of the fundus 7 to be measured can be adjusted. By reading the performed shifts by means of the measurement apparatuses 58, 59 as well as 68, 69 and 78, 79, or the corresponding electronic position signals, a base value for the lengths to be measured is obtained. The optical measurement now indicates the distance of the actual position of the reflection locations in the eye relative to the base position. Adding said actual position to the base value, the desired distance is obtained with high accuracy.

In addition to their associated partial optics 34, 35 and 36, the three reflection ray bundles 27, 29 and 31 remitted by the eye also illuminate the respective other partial optics and impinge on the detector array 43, defocused by the latter optics. This results in false light and thus to an undesired background. Since this false light, with the reference beams 53, 63, 73 focused there, is not adapted to the path difference, very high modulation frequencies are generated at the detector array, which are not resolved by the detector array. Nevertheless, in addition to increased noise due to aliasing, additional error signals may also appear. Therefore, it is advantageous to suppress this false light as far as possible. This is possible by spatial filtering in the image plane 40. For this purpose, a pinhole mask 80 is provided in this plane, said mask comprising three openings at the locations of the bundle foci. However, the positions of the bundle foci depend on the position of the eye 26—with the exception of the fundus bundle focus. Therefore, the eye has to be positioned by means of the above-described apparatus for observation of the position of the subject's eye. This allows good discrimination of the reflection ray bundles of the fundus 7 and of the cornea 5.

FIGS. 1 and 3 show the measurement of the positions of the anterior corneal surface, of the anterior lens surface and of the fundus. As already mentioned above, still further positions of eye structures can also be measured at the same time, however. For example, the posterior lens surface can be measured using the light virtually remitted from the $4^{th}$ Purkinje-Sanson image, or the position of the posterior corneal surface can be measured using the light virtually remitted from the $2^{nd}$ Purkinje-Sanson image. This requires corresponding additional reference ray bundles and partial relay optics (33) as well as additional orifices in the pinhole mask 80 and further array columns. However, for depths of the measurement field around 5 mm, it can be assumed that the two corneal positions are simultaneously present in the measurement signal.

Finally, the described interferometers can also be modified for measurement of other positions, such as the posterior lens surface. For this purpose, for example, the length of the reference beam 53 and the focal length of the optics 35 have to be reduced accordingly.

It should also be mentioned that the use of an array 43 comprising only three (431, 432 and 433) or four columns is not to be construed as a limitation. Commercially available array cameras often comprise several hundred columns. These may be used in two ways: on the one hand, several columns between the columns to be read out can be left unused to avoid optical and electronic cross-talk. Moreover, the line elements of several adjacent columns can also be connected to each other by binning, in order to increase the measurement sensitivity.

FIG. 2 shows a modification of the interferometer I of FIG. 1; therefore any elements taken from FIG. 1 without modification or with the same function are identified by the same reference numerals and shall not be explained here again. The difference between the constructions of FIGS. 1 and 2 is essentially that the spectrometer S now no longer uses a two-dimensional photodetector array, but three individual line photodetector arrays 531, 532 and 533. In order to divide the reflection ray bundles 31, 29, 27, which are spatially separated, for example, by pupil partition and are superimposed upon the reference beams 53, 63, 73, two suitable mirrors 540, 541 are provided in the detection branch D, said mirrors deflecting two of the reflection ray bundles having reference beams superimposed upon them, towards two photodetector array lines 531 and 533, which are perpendicular to the optical axis.

FIG. 6 shows an interferometer I, which has been modified further. In this case, too, any components taken from FIG. 1 without modification or with the same function are provided with the same reference numerals, so that a repetition of their description can be dispensed with. The interferometer I of FIG. 6 uses a type of spatial separation which differs from that of FIG. 1. The separation of the measurement beam M and the superposition of the three reference beams 53, 63, 73 is effected here by beam splitters. Any components which correspond to those of FIG. 1 in function or structure are provided with the same reference numerals and, where required, a suffix .1, .2 or .3 has been added to distinguish the components for the three individual superpositions. Thus, for example, the component 42.3 corresponds to the component 42 of FIG. 1; however, in the representation of FIG. 6, it is only effective for the superposition with the reference beam R3.

In the construction of FIG. 6, the separate superposition of the reflection ray bundles 27, 29, 31 in the measurement beam M is not effected here by relay optics 33 provided with a partitioned pupil, but by deflecting elements 33.1 as well as 33.2, which de-couple the reflection ray bundles 27 and 29 from the beam. The deflecting elements 33.2 and 33.1 can be provided, for example, as spectrally neutral beam splitters.

The deflecting element 33.2 deflects a portion of the measurement beam M out of the ray bundle, which has been split off by the beam splitter 25, and provides it for superposition with the second reference beam 63, which is coupled in separately via a beam splitter 66. The subsequently arranged optics correspond substantially to the optics of the detector branch D of FIG. 1, the difference being that no spatially separated pupil is present now; the beam path following the beam splitter 33.2 no longer guides any spatially separated beams. Accordingly, the photodetector array 43.2 need not sense along two dimensions.

The same applies to the photodetector array 43.3 which, after splitting off by the beam splitter 33.3, is located at the end of the beam path.

The portion of the measurement beam M still present following the beam splitters 33.2 and 33.3 has the reference beam 53 superimposed upon it and is detected at the photodetector array 43.1 after previous spectral decomposition.

Thus, the interferometer of FIG. 6 comprises three spectrometers, S1 for the remaining measurement beam M superimposed upon the reference beam 53 from reference beam path R1, the spectrometer S2 in the part of the beam path which has been split off by the beam splitter 33.2, into which part the reference beam 63 is fed, and the spectrometer S3, which is arranged following the beam splitter 33.3 and detects the separated radiation, upon which the reference beam 73 is superimposed.

The spatial separation by the beam splitters has the advantage that the pinholes 80.1, 80.2 and 80.3 can be designed to suppress false light much more efficiently. Also, separate focusing by means of the partial optics 36.1, 36.2 and 36.3, which are now easier to adjust individually, is possible without any problem, so that the signal/noise ratio for depth-separated object regions is improved.

FIG. 7 shows an interferometer I which, like the previously described interferometers, also follows the principle of individually superimposing a measurement beam M upon reference beams guided in reference beam paths R1, R2 of different lengths and detecting them. Any details realized with reference to the above-described figures are, therefore, also possible without restriction for the variants described hereinafter. Also, the same reference numerals are assigned to the same elements, so that their explanation can be omitted here. Further, in the following figures a distinction in terms of the reference beams and their beam paths or superpositions, respectively, shall be made also by adding a corresponding suffix .1, .2 etc.

The interferometer I of FIG. 7 separates the reference beam paths by polarization. For this purpose, a polarizer 300 circularly polarizes the radiation from the light source 1, before it is incident on the beam splitter 25 and, from there, on a sample P. Alternatively, a radiation source emitting circularly polarized light is used. In the reference beam path R, the circularly polarized radiation is divided by means of a polarization splitter 301 into two beams, which are polarized perpendicular to each other. The polarization splitter can be realized, for example, by a Wollaston prism. Adjustable gray filters 303.1 or 303.2, respectively, allow setting of the intensity of the radiation in the two reference beam paths R1, R2, which is advantageous for optimizing the measurement signal. The reference beams in R1 and R2 are reflected by reflectors 304.1 or 304.2, respectively. Each reflector 304 is displaceably mounted to a carriage 305, so that the path length of the reference beam path is individually adjustable. This can be effected under the control of a computer 200. The shifting mechanism can have the construction described, in particular, with reference to FIG. 1 et seq. The superimposed measurement beam M with the reference beams, which are superimposed upon each other in the back-reflection direction of the reference beam paths R1 and R2 following the polarization splitter 301, is detected in the detection arm D.

In the detection arm, the superimposed beams are divided again by a polarization splitter 302 so that superimposed beams 306.1 and 306.2 are present, in which the reference beams from R1 or R2, respectively, are superimposed upon the measurement beam M. As already described before, the different path lengths of the reference beam paths R1 and R2 cause a corresponding depth selection in the sample P which may be the human eye A again, for example. The superimposed beams 306 separated in this manner according to their polarization are then detected in a spectrometer S individually.

Finally, for spatial measurement of the sample P, a scanner 307 comprising suitable optics is also provided, said scanner scanning the sample with the incident radiation.

A possible design of the spectrometer S is shown by way of example in FIG. 8. For example, one polarization manipulator 308.1 or 308.2 each is arranged following the beam splitter 302, by which manipulator the direction of polarization of the respective beam can be rotated or adjusted such that a maximum yield is obtained in the subsequent beam path. The polarization-separated beams 306.1 and 306.2 fall on the diffraction grating 42.1 or 42.2, i.e. on a reflection diffraction grating, after having passed the polarization manipulator 308.1 or 308.2. The spectral division thus obtained is then detected in detector array lines 43.1 or 43.2.

The spectrometer S is composed of two individual spectrometers S1 and S2, which individually detect the polarization-separated superimposed radiation 306.

Whereas FIGS. 1-6 individually superimpose and detect by spatial separation, the construction of FIG. 7 uses polarization separation.

As already mentioned, FD OCT can work in two ways. On the one hand, a short-coherence radiation source can be used as previously described. This will require spectral decomposition of the superimposed radiation. On the other hand, a spectrally sweepable short-coherence radiation source can be used. If the wavelength of this source is swept through the spectral range, no spectral analysis of the radiation is required anymore; instead, a spectrally insensitive detector can be used. The sample structure can be obtained in both cases by forming the inverse Fourier transform of the spectral interference pattern. Of course, the interferometers I explained above and also below can be adapted to any of the two modes of operation. The required modifications are indicated by way of example in FIG. 9 for the interferometer I of FIG. 7. Now, instead of the spectrometers S1 and S2, it is merely required to arrange individual detectors 309.1 and 309.2 following the polarization beam splitter 302, which detectors do not perform a spectral analysis of the incident radiation. In the variant according to FIG. 9, the construction of FIG. 7 can also be employed for TD OCT. This will merely require synchronized adjustment of the path length of the reference beam paths R1, R2, and tuning of the wavelength of the light source 1 will become unnecessary.

FIG. 10 shows a modification of the construction of FIG. 7, wherein spatial separation of the reference radiation R1 and R2 and the corresponding superposition are not effected by polarization, but by spectral separation. Therefore, two light sources 1.1 and 1.2 are provided which emit radiation at different wavelengths, as shown in FIG. 11. In the spectrum plotted therein, the wavelength distribution on the left is to be assigned, for example, to the light source 1.1 and the wavelength distribution on the right is present in the radiation of the light source 1.2. The remaining construction of the interferometer I of FIG. 10 corresponds to that of the interferometer of FIG. 7, except that the polarization splitters are no longer required, while two spectrally distinct beams propagate through the interferometer. The spatial separation indicated for the sake of clarity does not absolutely have to be present in the entire beam path; where applicable, suitable non-dichroic splitters can be used. The construction may then correspond substantially to that of FIG. 7, with the polarization splitters 301 and 302 replaced by correspondingly dichroic splitters and the polarizer 300 substituted by a corresponding superimposing unit for the spectrally distinct beams.

FIG. 12 shows the construction of the spectrometer S, which detects the two spectrally distinct beams 306.1 and 306.2. Again, for the sake of clarity, a spatial distance between the beams 306.1 and 306.2 is indicated, although it need not be present. The diffraction grating 42 divides the two superimposed, spectrally distinct beams into different spatial angles, so that they can be directed onto separate photodetector arrays 43.1 as well as 43.2. In the construction of FIG. 12, a deflecting mirror 310 is additionally provided to expand the beam path.

In case of the light sources 1.1 and 1.2 being swept, the spectral analysis can be dispensed with again and only the spectrally insensitive detectors 309.1 or 309.2 are required. For this purpose, however, the superimposed beams 306.1 and 306.2 have to be spatially separated by suitable means known to the person skilled in the art.

Of course, instead of two independent light sources 1.1 and 1.2, a single light source can also be used which simultaneously emits two chromatically different beams. FIG. 14 shows a further modification of the spectrometer of FIGS. 1-10, but now measurement and superposition of reference beam paths R1, R2 etc. are not effected simultaneously, but sequentially. The design substantially corresponds to that of FIG. 7, although no elements having a polarizing effect are used.

Instead, the reference beam path R comprises several beam splitters 311, which split the beam path into several reference beam paths R1, R2, . . . , each terminating in corresponding reflectors 304. Each reflector 304 is mounted to a carriage 305. In the exemplary embodiment, three different reference beam paths R1, R2, R3 are formed. An aperture wheel 312 is arranged following the beam splitters 311.1, 311.2 or 311.3, respectively, said aperture wheel 312 realizing a selecting means that defines which of the reference beam paths R1, R2, R3 is active. The others are switched off. In the representation of FIG. 14, the reference beam path R1 is active, i.e. its reference beam is reflected by the mirror 304.1. By rotating the aperture wheel 312, a reference beam having a different length is activated in each position, so that the superimposed beam 306 is always formed by superposition of the measurement beam F and the reference beam from the correspondingly activated reference beam path. The spectrometer S then detects the corresponding signal. As already mentioned, the length of the reference beam paths R1, R2, R3 (of course, any number of reference beam paths can be used) causes the depth selection of the object region in the sample P.

If a broadband light source 1 is used for the interferometers described above or below, the spectrometer(s) S is (are) preferably realized according to the so-called Czerny Turner design. If the sample P or the eye A, respectively, is illuminated by several spots or by an illumination line, which is possible for all constructions described here, the spectrometers S are provided with suitable detector arrays, which record the spectral interference pattern on different detector array lines.

In the case of a spectrally swept light source 1, photodiodes or monochromators which usually are most sensitive to the swept spectral range of the light source 1 are suitable instead of the spectrometers S, as already mentioned. If several spots or a line in the sample P are illuminated, the detector is again equipped with the suitable number of photodiodes or pixels.

Basically, the photodetector has to record the interference pattern synchronously with the sweeping of the light source. This is effected by suitable control of the computer 200, which is an exemplary realization of a control device controlling operation of the interferometer I.

In particular, the control device enables fully automatic two- or three-dimensional image acquisition.

FIG. 15 shows a variant of the spectrometer of FIG. 7, wherein the eye is now illuminated by a double beam. Elements already described in FIG. 7 are, therefore, not described here again. The double beam provides two measurement beams M1 and M2, which are polarized perpendicular to each other, said beams extending coaxially and being mutually offset. Thus, the interferometer I of FIG. 15 uses two measurement beams M1 and M2 and two reference beams R1 and R2. This easily enables two simultaneous measurements, for example, of the position of the cornea and of the position of the fundus. Further, splitting the double beam by means of polarization splitters 313, 314 and deflecting mirrors 315, 316 allows separate focusing of the two measurement beams M1 and M2. This merely requires moving a focusing element into the bypass path between the polarization splitters 313 and 314. For example, this allows to focus the measurement beam M1 onto the anterior surface of the eye, whereas the measurement beam M2 is parallely incident and, thus, focused in the fundus through the eye lens. The eye length L is obtained as the sum of the offset (=the path difference) of the two measurement beams M1 and M2 due to the beam division by the beam splitters 313 and 314, plus the path difference of the reference beams R1 and R2, plus any still remaining optical path differences, which result from the difference of the positions of the signal peaks of the two Fourier transforms of the two K spectra.

FIG. 16 shows a modification of the interferometer I of FIG. 15, wherein only one spectrometer S is now provided for the two measurement beams M. For this purpose, the sum of the path differences between the two measurement beams M1 and M2 and the respective reference beams R1 and R2 is suitably set to values of less than the measurement field depth z. The eye length then results, as already described for FIG. 15; the difference between the positions of the two single peaks of the two Fourier transforms is read out on the computer monitor. The setting can be achieved by setting the path differences by an adjusting mechanism, for example a shifting mechanism of the type previously described for other interferometers, either on the respective measurement beam or reference beam.

An alternative consists in using a measurement beam as the reference beam and suitably setting the optical path length of the beams such that, again, two measurement signals, i.e. the autocorrelation function (ACF) of the reference beam and the interference signal, are displayed on the computer monitor. The eye length now results as the sum of the path difference between the two beams plus the position difference of the two Fourier transforms which is read on the monitor. Accordingly, the apparatus is insensitive to movements of the measurement object.

For measurement of the eye length it is advantageous to reference the interference pattern with respect to the path length difference to the anterior corneal surface. This can be achieved by the reference beam path using a reflection from the cornea, i.e. the reference ray bundle being reflected by the cornea. A suitable design is shown in FIG. 17. Any components taken from the previously described interferometers I without modification or with the same function are again referred to by the same reference numerals here and shall not be explained again.

The beam path of FIG. 17 is that of a short-coherence interferometer I, which directs onto the eye a double beam consisting of two beams 400, 401, being coaxial to each other and mutually offset. The leading beam 401 acts as reference beam, which is reflected at the anterior corneal surface. The path length difference between the beams 400 and 401 is adjusted by means of mirrors 318 and 319, onto which the beams are directed via a beam splitter 317. The path length difference substantially corresponds to the expected eye length L. The pre-set path length difference ensures that the reference beam 401 interferes with the measurement beam 400 reflected by the fundus, so that the spectrometer arranged following a beam splitter 322 records a corresponding interference signal. A Fourier evaluation of the signal then shows, on the one hand, the autocorrelation function of the reference beam 400, which interferes with itself, and on the other hand, a corresponding distance for superposition of the reference beam 401 with the measurement beam 400. In addition the path length difference Z, which has been set externally, also has to be taken into consideration. The length L of the eye A, thus, results from the sum of the measurement reading of the optical measurement plus the mechanically set path length difference between 400 and 401. The pre-setting allows the FD analysis with simple means for a comparatively large range of measurement.

The interferometer of FIG. 17 is an example, wherein the reference beam is reflected by the sample. This automatically achieves a relative measurement, and the distance is not determined from the difference of two absolute points of measurement. Space variants of the sample, thus, become negligible.

FIG. 18 shows a fiber-optical design of the interferometer I of FIG. 17. Again, any components adopted without modification or with the same function are referred to by the same reference numerals. The beams 400, 401 are now formed using a coupler 323, which feeds two fibers emitting the reference beam 401 and the measurement beam 400. The reference beam 400 is adjustable in terms of path length by a shifting mechanism as already described above, for example, with reference to FIG. 1. In addition, however, optics 320 are also arranged on the shifting mechanism, so that shifting automatically also results in suitable focusing on the cornea 5. Further, dispersion compensation prisms 54' and 54" are incorporated in the shifting mechanism such that a change in the length of the light path automatically also results in a correspondingly adapted, i.e. dynamic, dispersion compensation. Otherwise, the design functionally corresponds to that of FIG. 17.

The monitor image 201', which is represented after evaluation by the computer 200, is additionally shown for ease of understanding. It is also evident from FIG. 18 that the measurement beam M1, which simultaneously acts as reference beam R, is focused on the anterior corneal surface. Thus, a dynamic focus is achieved which can be adapted to different eye lengths. Due to the shiftable optics 325, the measurement beam M2 is collimated such that the optical effect of the eye A focuses the measurement beam M2 on the fundus 7.

In the case of reduced requirements concerning signal quality, the beam separation apparatuses can be simplified, in which case there are several measurement signals simultaneously at the array and in the Fourier transform. Such beam paths are depicted in FIGS. 19 and 20 as simplifications of the beam paths of the design according to FIG. 16. The reference mirror 304.2 is now mounted in both arrangements on a shifting table 304.4. By moving this shifting table, the synchronous movement of the respective signal peak of the Fourier transform shows which sample surface said peak belongs to.

In FIG. 20, the reference mirror 304.1 is replaced by a partially transmitting mirror 304.3. Additional partially transmitting reference mirrors can be arranged between the beam splitter 25 and the reference mirror 304.2. Thus, two or more reference beams in the reference beam path can be used simultaneously and several measurement regions spaced apart in a depth direction can be detected. These further reference mirrors can be mounted to shifting tables in order to increase the flexibility of measurement.

The design of FIG. 20 can be additionally modified. The spectrometer S then includes a detector array 43 comprising at least 7,000 pixels, for example 8,000. In this case, only one measurement beam will be used and the partially transmitting mirror 304.3 can be omitted. Thus, only one reference beam path R will be present in the interferometer I. The eye length measurement is effected as a single measurement by the high pixel number array 43 in combination with suitable spectral spreading through the diffraction grating 43.

In FIG. 24, a light source typically used in short-coherence interferometry, for example a superluminescence diode, is identified by 201. A light-conducting fiber 202 guides radiation to a collimator 203, which collimates light bundles 204 output by the light-conducting fiber. The bundles 204 are guided through a beam splitter 205 and reflected via a deflecting mirror 206 to a beam splitter 207 to form a measurement beam 215. Together with mirrors 208 and 209, the beam splitter 207 forms a Michelson interferometer 210, which generates a double beam 211 that is directed onto an eye 213 through a beam splitter 212. The light waves reflected and scattered back by the interfaces of the eye 213 are reflected from a beam splitter 212 to a beam splitter 214, from which they are reflected to a spectrometer 216.

The light bundle 217 reflected by the beam splitter 205 falls on a beam splitter 218 which, together with mirrors 219 and 220, forms an additional Michelson interferometer 221 generating a double reference beam 222 that is also reflected by the beam splitter 214 to the spectrometer 216. The spectrometer 216 consists of a reflection grating 223, spectrometer optics 224 and a linear detector array 225. Alternatively, a spectrometer comprising a transmission grating or any other dispersive element can be used.

Intraocular distances are measured such that the two reference mirrors 219 and 220 are shifted, for example using stepping motor- or piezo-motor-controlled positioners 219' and 220', so as to visualize the signal peaks of the very boundaries in the measurement field which define the distance to be measured (cf. FIG. 21). For example, for the measurement of the eye length L indicated in FIG. 21, $$L=S+(R'-R)-(C'-C)$$

holds true.

In FIG. 25, part of the interferometer of FIG. 24 has a fiber-optical design (any structurally or functionally unmodified components generally bear the same reference numerals in the figures). Here, the light emitted by the short-coherence light source 201 is guided from a light-conducting fiber 230 to a coupler 231, which divides it into a measurement beam and a reference beam, which are guided through fibers 232 and 233 as well as collimators 234 and 235 to the interferometers 210 and 221, respectively. The remaining beam path corresponds to that of FIG. 24.

In FIG. 26, the short-coherence interferometer is equipped with a double spectrometer 240 which consists of two identical diffraction gratings 242 and 243, a beam splitter 214, which combines the beams diffracted at the gratings 242 and 243 in this case, and the linear detector array 225. The light waves reflected and scattered back from the eye 213 are diffracted by the diffraction grating 242, and the double reference beam 222 is diffracted by the diffraction grating 243; both diffraction images superimpose their diffraction images on the linear detector array 225. It is required to adjust the diffraction gratings 242 and 243 by observation from the array side such that their images are congruent. The short-coherence interferometer illustrated in FIG. 6 then works exactly in the same manner as that of FIGS. 4 and 5. The detector array 225 registers the real intensity I(k) of the (complex) frequency spectrum Î(k) of the radiation at the interferometer output.

The diffraction grating 243 of the double spectrometer 240 is connected to a piezoelectric actuator 245, which can shift said diffraction grating 243 in the grating plane normal to the grating lines by ¼ of the grating constant (double arrow 246). The waves diffracted at the grating will thus be subjected to a phase shift of $\pi/2$. In this position, the detector array 225, therefore, registers the quadrature component associated with the real intensity I(k), by which quadrature component the complex frequency spectrum Î(k) of the radiation at the interferometer output is obtained according to the above equation.

Analogously, the grating 242 can be shifted by ¼ of the grating constant, too. Alternatively, an electro-optical phase modulator 244 in the double reference beam 222 can generate a phase shift of the reference beams. Such phase modulator 244 can also be arranged in the double measurement beam 241. However, whereas the grating method is independent from the wavelength, this is not the case for the phase modulator method; the latter method can be used at wavelength bandwidths of up to several 10 nm.

FIG. 27 shows an arrangement for measuring partial lengths in the eye by means of Fourier domain interferometry, which selectively uses the retinal pigment epithelium (RPE) for axial length measurement and discriminates, by polarization-optical methods, the light scattered back from the other retinal layers. For this purpose, a linear polarizer 251 is located in the light bundle 204 emitted by the collimator 203. Said linear polarizer 251 ensures a defined polarization condition of the light bundle 204 which illuminates the short-coherence interferometer. Further, a $\lambda/4$ plate 252 is arranged at 45° to the polarization plane in each partial reference beam 253 that interferes with the light reflected by the fundus of the eye 213. This produces circularly polarized light which reverses its direction of rotation by reflection at the reference mirror 219. By passing through the $\lambda/4$ plate 252 once more, linearly polarized light is formed again, which now has a polarization plane rotated by 90°, i.e. normal to the original polarization plane. In the case of light polarized normal to the original direction, only light reflected by the RPE and having a modified direction of polarization leads to interferences. Thus, the distance between the anterior corneal surface and RPE, i.e. an axial length measurement of the eye, is obtained on the basis of the RPE.

By rotating the $\lambda/4$ plate (double arrow 255) about an axis 253' parallel to the axis of the beam 253, the component of the light polarized in parallel with the original polarization plane can be modified. This sets the strength of the interferences with the light reflected by the fundus, and in addition to the RPE, other boundary layers of the retina can also be made visible.

Analogously, the polarization plane of the beam 253 can be rotated using a $\lambda/2$ plate instead of the plate 252, said $\lambda/2$ plate being rotatable about the beam axis 253'. This changes the strength of the interferences with the light reflected by the fundus.

Further adaptations to different measurement conditions are possible by the auxiliary devices mentioned in FIG. 28, which can generally be arranged in or reflected into the measurement beam path and, in particular, in the double measurement beam 211:

A lens group 280 consisting of two cylindrical lenses 281 and 282 having opposite refractive powers can be used to compensate for an astigmatism of the subject's eyes. By rotating their cylindrical axes about the axis of the measurement beam (e.g. 211) relative to each other (double arrow 283), different cylindrical refractive powers of the lens group can be achieved. Rotating the entire lens group (double arrow 284) about the axis 211' of the measurement beam allows to modify the orientation of the cylindrical axis of the group. Using this auxiliary device, an astigmatism reverse to that of the subject's eye can be induced in the measurement beam and the subject's astigmatism can be compensated for.

Zoom optics 286 (for example comprising a shiftable—double arrow 287—scattering lens 288 between two collective lenses 289 and 290) can be used to compensate for an ametropia of the subject's eye. These zoom optics have a central position with a refractive power of zero and can generate both positive and negative refractive powers. Using a beam splitter 292, a refractometry apparatus, for example a Hartinger coincidence refractometer (open arrow 293) can be reflected in. Analogously, a fixing light (arrow 295) can be reflected in by a beam splitter 294 in order to fixate the axis of vision of the subject's eye 213. The fixing light may have a different color (for example green). It may also be emphasized by blinking. A positionally shiftable fixing light can be used to fixate or vary the line of vision.

The group 300 consists of two wedges 301 and 302 which are shiftable relative to each other (double arrow 297). This leads to a deviation of the measurement beam (e.g. 211), the amount of said deviation being variable by the amount of the relative prism shift and its direction, by rotation (double arrow 103) of the prism group about the axis 211' of the double measurement beam 211. Thus, the optical axis of the fixed eye can be adjusted parallel to the beam axis 211' of the measurement beam in order to obtain optimal light reflections from the eye.

Zoom optics 310 serve to effect measurements on the anterior chamber of the subject's eye. They are designed such that their refractive power is adjustable from zero up to several diopters. The measurement beam (e.g. 211) is focused in or near the anterior chamber by these optics, thereby increasing the signal strength of the light components reflected by the anterior chamber. However, excessive focusing requires very careful adjustment and maintenance of the transverse position of the eye, which is difficult. Therefore, the optimum will be found where focusing is less strong, which has to be empirically determined by suitable adjustments of the zoom optics 310. For this purpose, these zoom optics can comprise, in addition to a refractive power adjustment (double arrow 311), also a means of adjusting their position in the direction of the optical axis of the measurement beam (double arrow 312). Also, instead of the zoom optics, optics 313 having a corresponding fixed refractive power can be swiveled into the beam path (double arrow 314) and can also be arranged to be shiftable in the direction of the optical axis 211'.

The above-mentioned auxiliary devices can all be jointly arranged in the measurement beam path (for example the double measurement beam 211). Alternatively, these devices can also be arranged individually or in groups, of course. However, group 300 generally requires separate fixing of the eye 213 and should, therefore, only be used together with the fixation of the eye by the components 294 and 295. Since the subject sees a red measurement beam (e.g. 211) at the wavelengths typically used here, a different color, for example green, is advantageous, as mentioned, for the light reflected in.

It should also be mentioned that, in addition to the configuration of an FDI according to FIG. 24, the other configurations can also be fiber-optically modified with analogy to FIG. 25.

The methods according to the invention were described in the above text with reference to the measurement of the axial length of the eye. However, it is explicitly pointed out here that these methods can also be employed to measure other intraocular distances, such as the corneal thickness, the anterior chamber depth and the lens thickness. For this purpose, the reference mirrors 219 and 220 merely have to be shifted to such positions that the corresponding reflections become visible in the two windows of measurement. Length measurement is effected in an analogous manner as described above in connection with an equation.

The invention claimed is:

1. An apparatus for interferometric measurement of a sample, the sample comprising an eye, the apparatus comprising:
   a short-coherence interferometer arrangement, which comprises a measurement beam path through which a measurement beam is incident on the sample, and a reference beam path, through which a reference beam passes wherein the measurement beam is superimposed on the reference beam and interference occurs between the reference beam and the measurement beam; and
   a spectrometer arrangement that detects the superimposed beams, said arrangement comprising an element which spectrally spreads the superimposed beams and a detector array which comprises at least 7,000 individual photo-sensitive cells arranged such that two signal peaks are captured in a short period of time, one of the two signal peaks representing an anterior structure and another of the two signal peaks representing a posterior structure and such that eye measurements over a full axial length of the eye are performed in the single measurement over a short period of time.

2. A method for short-coherence interferometric measurement of a sample, the sample comprising an eye, the method comprising:
   directing a measurement beam onto the sample through a measurement beam path;
   superimposing a reference beam passing through a first reference beam path onto the measurement beam and wherein interference occurs between the measurement beam and the reference beam;
   using a spectrometer arrangement for detection of the superimposed beams, said spectrometer arrangement comprising an element which spectrally spreads the superimposed beams and a detector array which comprises at least 7,000 individual photo-sensitive cells;
   capturing two signal peaks in a short period of time, one of the two signal peaks representing an anterior structure and another of the two signal peaks representing a posterior structure; and
   thus performing eye measurements over a full axial length of the eye in the single measurement over a short period of time.

* * * * *